United States Patent [19]

Borkan

[11] Patent Number: 4,612,934
[45] Date of Patent: Sep. 23, 1986

[54] NON-INVASIVE MULTIPROGRAMMABLE TISSUE STIMULATOR

[76] Inventor: William N. Borkan, 3364 NE. 167th St., N. Miami Beach, Fla. 33160

[21] Appl. No.: 631,299

[22] Filed: Jul. 16, 1984

Related U.S. Application Data

[63] Continuation-in-part of Ser. No. 278,991, Jun. 30, 1981, Pat. No. 4,459,989.

[51] Int. Cl.$^4$ ............................................. A61N 1/36
[52] U.S. Cl. .................................................... 128/421
[58] Field of Search ............... 128/419 C, 421, 419 E, 128/419 R, 422, 423 R

[56] References Cited

U.S. PATENT DOCUMENTS

| | | | |
|---|---|---|---|
| 3,236,240 | 2/1966 | Bradley | 128/419 E |
| 3,727,616 | 4/1973 | Lewzkes | 128/422 |
| 4,019,518 | 4/1977 | Maurer et al. | 128/419 R |
| 4,044,775 | 8/1977 | McNichols | 128/421 |
| 4,390,756 | 6/1983 | Hoffman et al. | 128/421 |
| 4,399,821 | 8/1983 | Bowers | 128/421 |

Primary Examiner—William E. Kamm
Attorney, Agent, or Firm—Barnes & Thornburg

[57] ABSTRACT

An electronic tissue stimulator system is provided comprising a plurality of electrodes to be implanted adjacent tissue to be stimulated in a patient. A transmitting means transmits stimulation pulses for stimulating the electrodes and programming data defining which of the electrodes are to be stimulated and the electrical polarity of the electrodes relative to one another. A receiving means to be surgically-implanted within the patient which receives the stimulation pulses and the programming data, and delivers the energy in the stimulation pulses to the electrodes as defined by the programming data. Using an internal voltage source, only the programming data need be transmitted which define electrode selection and polarity and stimulation pulse parameters. Physical parameters can be measured and used to modify programming data. Dose periods are defined by programming data and/or a combination of programming data and physical parameter measurements.

9 Claims, 34 Drawing Figures

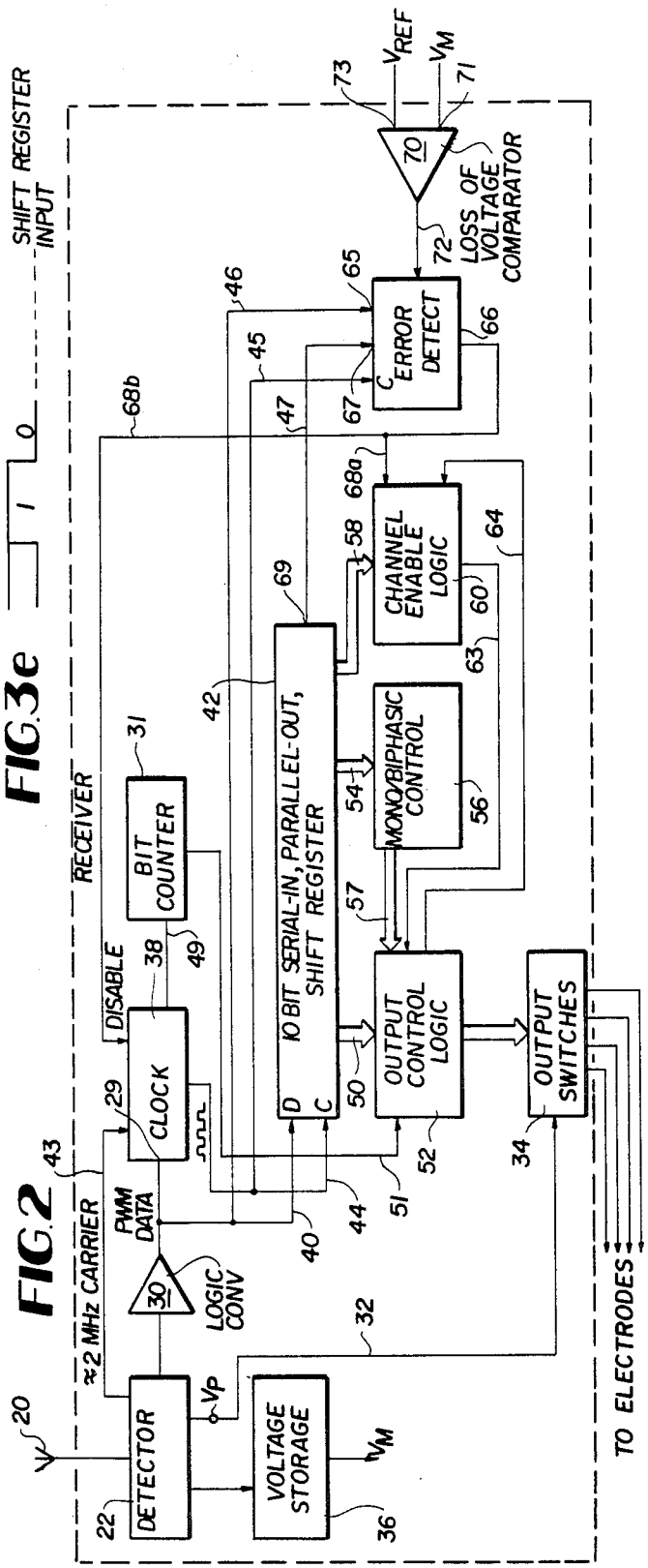

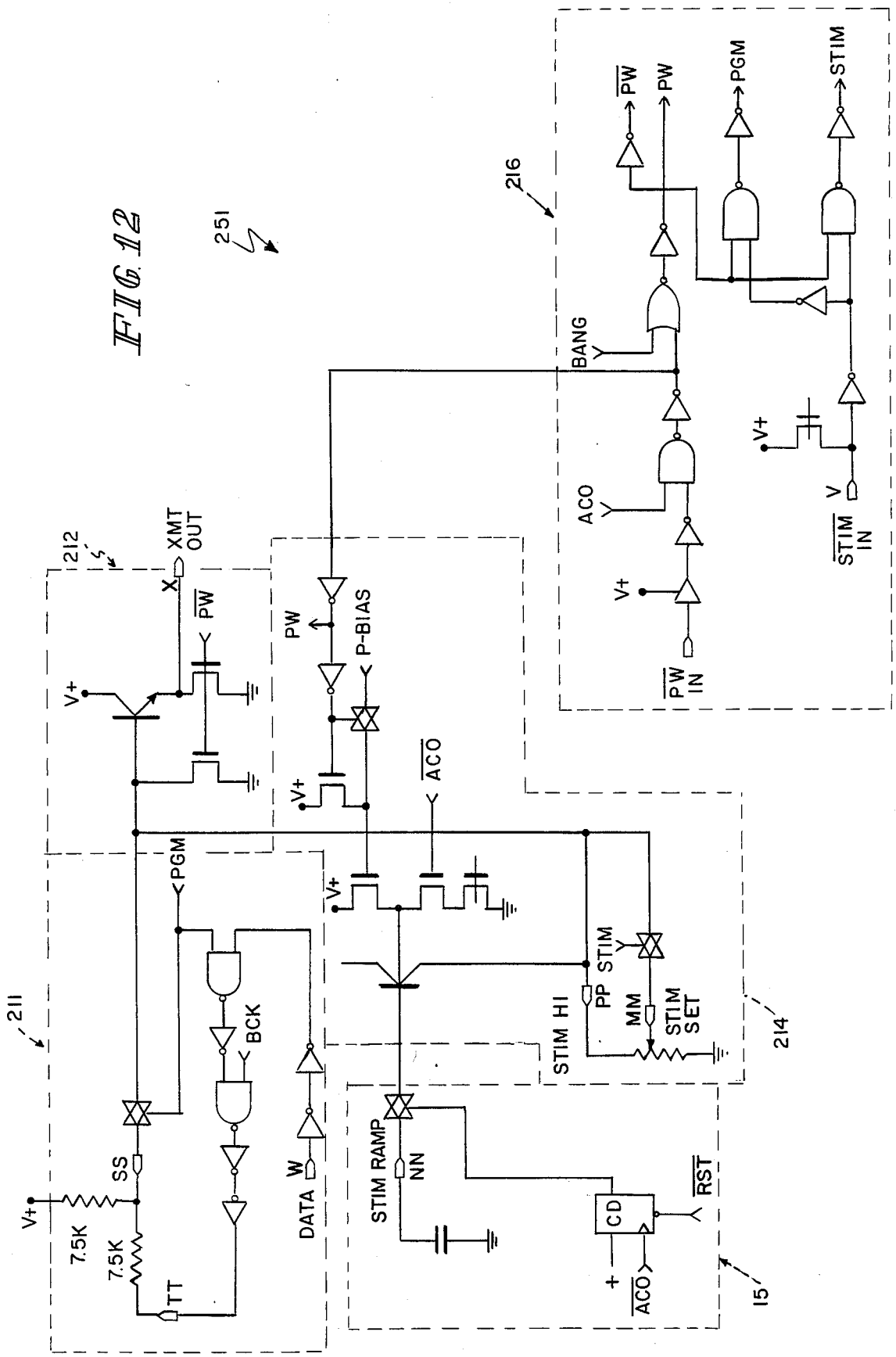

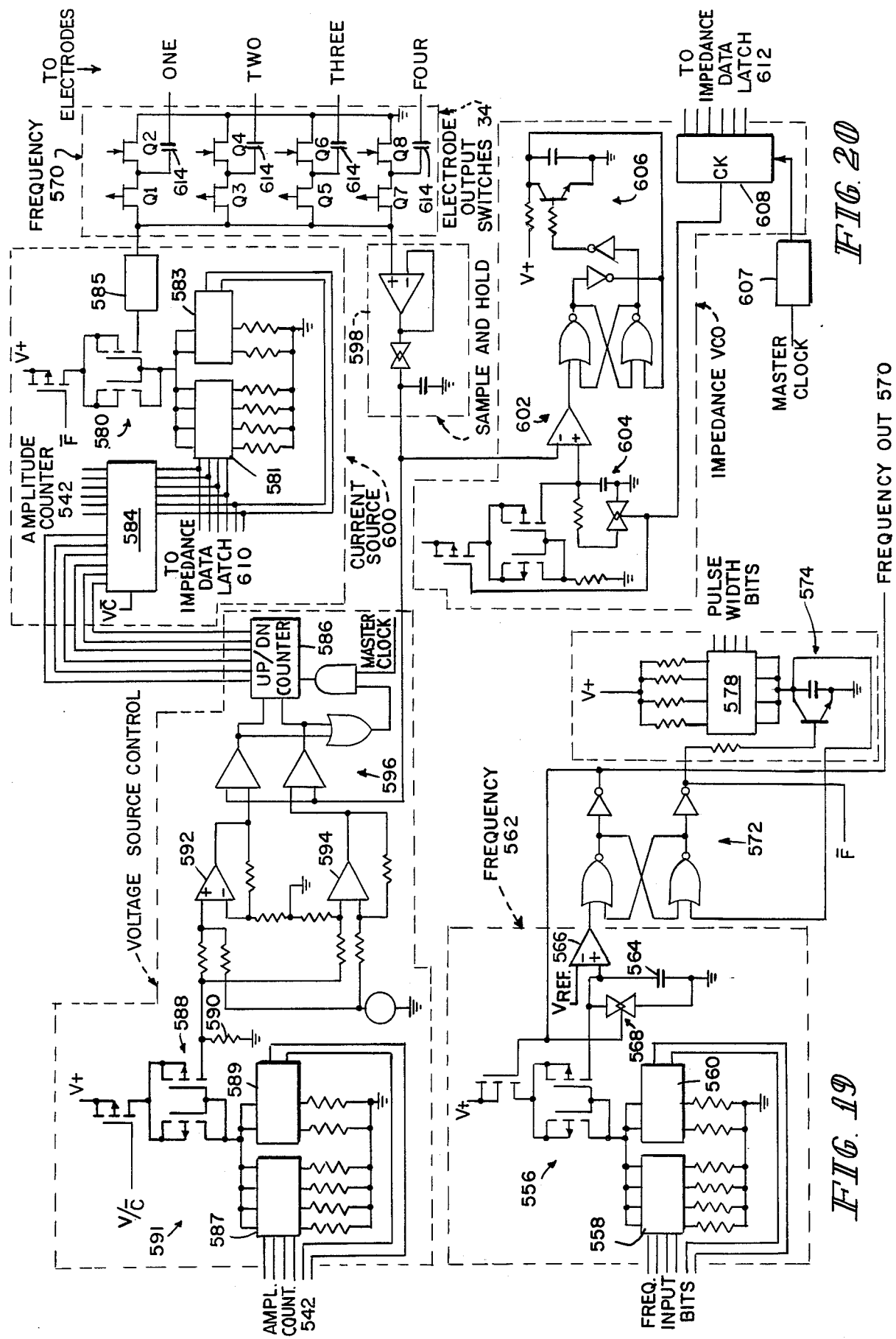

EXTERNAL PROGRAMMER
FRONT VIEW

NON-INVASIVE MULTIPROGRAMMABLE TISSUE STIMULATOR

BACKGROUND AND SUMMARY OF THE INVENTION

This is a continuation-in-part of Ser. No. 278,991 filed 6-30-81 now U.S. Pat. No. 4,459,989 issued July 17, 1984.

This invention relates to a partially implanted electronic tissue stimulator system for controlling various neurological and muscular disorders.

The concept of using an electronic stimulation system for the purpose of controlling a nerve or muscle response is well known. This type of system typically utilizes a pulse generator which remains outside the patient's body. A transmitting antenna receives RF energy from the pulse generator and transmits this energy through the patient's skin to a subcutaneous receiver. The receiver provides signal processing of the received pulses and transmits the energy derived therefrom to activate a pair of electrodes implanted adjacent nerve or muscle tissue. The receiver may be powered internally by an electrical supply such as a rechargable battery pack or in the preferred method, by the energy in the transmitted pulses. A system like the one described above is seen in U.S. Pat. No. 3,727,616. It is also known in the prior art to provide a plurality of electrode pairs adjacent a nerve center such that the potential differences between the electrodes and the number of electrode pairs which are energized controls the number of nerve fibers that are stimulated. Such a system is described in U.S. Pat. No. 3,499,768.

A problem arises, however, in these prior art systems, when the electrode placement fails to provide the desired physical response. This failure may also be caused by improper polarity of the stimulated electrodes relative to one another. Furthermore, it is often required that the electrodes be implanted surgically adjacent to one or more nerve fibers. This type of procedure involves inherent risks due to the fact that it is often performed in close proximity to the brain or spinal cord. It is therefore desirable to perform the electrode implantation only one time to minimize the surgical risks to the patient as well as the financial burden. Moreover, even when a plurality of electrodes have been utilized, such that repeated surgical procedures are not required, the prior art systems have not provided for dynamic programming of different electrodes after surgery such that the physician can find the appropriate electrodes that produce a desired response.

The prior art systems have also proven to be somewhat ineffective in practice due to their inability to provide more than one type of stimulation signal to the electrodes. Specifically, in the event that the chosen signal does not provide appropriate treatment, another surgical procedure must be performed to implant a unit which can provide a different type of stimulation signal. Further, even patients who respond to one type of signal might respond better if another type were used, however, the prior art systems do not generally allow the physician such flexibility. Therefore, even though a different stimulation signal might be more beneficial to the patient, the physician will not usually perform additional surgery unless there is no positive response.

The problems of the prior art systems have severely hampered the widespread application of tissue stimulation systems to date, even in areas where they show great promise in relieving disorders which have no other viable treatment alternatives.

It is therefore an object of the present invention to provide a partially implanted tissue stimulator system wherein the subcutaneous receiver can be non-invasively programmed any time after implant to stimulate different electrodes or change stimulation parameters such that a desired response can be attained. Each electrode is capable of assuming a positive, negative or open-circuit or high impedance status with respect to the other electrodes.

It is another object of the present invention to provide a tissue stimulator system wherein the electrode programming is derived from programming data which is modulated on a carrier wave. The carrier wave is then transmitted in bursts which define the stimulation pulses for the electrodes.

It is a further object of the present invention to provide a system of the type described wherein the receiver includes circuitry for determining whether the programming data is being received properly. The stimulation pulses are applied to the electrodes only after a predetermined number of consecutive, identical programming data sequences have been received.

It is yet another object of this invention to provide a system of the type described wherein the receiver may not require any internal source of electrical power.

It is still another object of this invention to provide a tissue stimulator system wherein the programming data is retained in the receiver between the reception of stimulation pulses unless the receiver is being reprogrammed or the transmitter is turned off.

It is still another object of this invention to provide a tissue stimulator system wherein the relative polarity of the stimulated electrodes can be kept constant or be alternated durin application of consecutive stimulation pulses to the electrodes.

A still further object of the present invention is to provide a tissue stimulator system wherein the stimulation pulse and/or electrode selection may be modified depending upon sensed physiologic parameters and electrode impedance.

An even still further object of the present invention is to provide a tissue stimulator system which as the capability of thereapeutic dosing.

These and other objects of the invention are attained by providing a plurality of electrodes to be implanted adjacent tissue to be stimulated in a patient. A transmitting means transmits stimulation pulses for stimulating the electrodes and programming data defining which of the electrodes are to be stimulated and the electrical polarity of the electrodes relative to one another. A receiving means to be surgically implanted within the patient receives the stimulation pulses and the programming data, and delivers the energy of the stimulation pulses to the electrodes as defined in the programming data.

As an alternative, the programming data may provide not only the selection of the electrodes and their relative polarity, but also may provide the parameters of the stimulation pulses. The programming data would include the frequency, amplitude and pulse width of the stimulation pulses which are generated in the receiver implant. Also, the programming data may include therapeutic dose capability which defines the dose period of stimulation. This allows the implanted stimulator to stimulate the tissues for a given period of time and be off for a given period of time. Sensors are provided to sense and measure physical and physiologic parameters to be used to modify the programming data. These parameters may include physiologic conditions of the tissue to be stimulated as well as electrode impedance. The programming data may be modified based on these measured parameters by a logic or microcomputer in the implanted receiver or at the external programmer. If the modification is done at the external transmitter, means are provided to transmit the parameter information to the external programmer. The programming data modification may be directed to the dose period, stimulation pulse configuration, or electrode paraselection.

The programming data is transmitted as a modulated signal on a carrier wave, the carrier wave being transmitted in bursts which define the stimulation pulses. The parameters of the bursts can be varied by the transmitting means such that the stimulation pulses have different pulse parameters. The receiving means includes detector means to demodulate the stimulation pulses from the carrier wave and logic converter means for separating the programming data from the stimulation pulses.

The receiving means further includes an error detection means for comparing consecutive sequences of programming data and controlling delivery of the energy in the stimulation pulses to the electrodes as a function of the comparison, this delivery defining a stimulation mode. In the preferred embodiment of the invention, this energy is delivered to the electrodes after a predetermined number of consecutive, identical sequences of the programming data are received by the receiving means. The receiver is in a programming mode prior to receiving the identical sequences. The receiving means further includes a voltage storage means for storing the steady-state energy derived from the stimulation pulses. Also, a loss of voltage comparator means is provided which continuously compares the energy in the voltage storage means with a predetermined voltage to control the error detection means. The loss of voltage comparator means resets the error detection means when the energy in the voltage storage means is less than the predetermined voltage, this reset serving to return the system to a programming mode.

The receiving means further includes a channel enable means controlled by the programming data and the error detection means for preventing energization of the electrodes until:

(a) the error detection means determines that a predetermined number of consecutive, identical sequences of the programming data have been received, (b) one of two redundant receivers in the receiving means has been selected for operation, and (c) no invalid electrode programming combination which would short the receiving means is defined in the programming data.

The receiving means further includes a memory means, which may be volatile or non-volatile, for storing the programming data and a mono/biphasic control means connected to the memory means for controlling the relative polarity of the stimulated electrodes during application of consecutive stimulation pulses. Also, the receiving means includes an output control logic means connected to the memory means, the output control logic means being controlled by the channel enable means. A plurality of output switches are connected to the output control logic means and are controlled by the programming data to deliver the energy in the stimulation pulses to the electrodes.

The receiving means further includes a delay means for controlling the output control logic means to delay the application of the stimulation pulses to the output switches. A clock circuit means is provided for controlling the delay means and for applying the programming data to the memory means. The period of the delay means is at least equal to the period of a programming data sequence such that the stimulation pluses are not applied to the output switches until after the programming data sequence has been stored in the memory means.

The receiving means may be powered by the energy transmitted by the transmitting means, or alternatively, by an internal energy source, or a combination of both sources.

The invention also contemplates a method of providing tissue stimulation comprising the steps of surgically-implanting a receiving means in the patient, surgically-implanting a plurality of electrodes connected to the receiving means adjacent tissue to be stimulated in the patient, selecting first programming data defining which of the electrodes will be stimulated and the electrical polarity of the electrodes relative to one another, and transmitting the first selected programming data to the receiving means to produce a response. Should the first programming data fail to produce a desired response, the method further provides for: selecting second programming data, different from the first programming data; defining a new combination of electrodes to be stimulated or a new polarity of the stimulated electrodes; and transmitting this second selected programming data to the receiving means. The method further provides for trial of various electrode combinations and polarities at various stimulation pulse frequencies, widths, and amplitudes such that the appropriate combination of these parameters may be combined to provide a desired response.

BRIEF DESCRIPTION OF THE DRAWINGS

FIG. 1 is a simple block diagram of the overall system of the invention.

FIG. 2 is a block diagram of the receiver of the invention.

FIGS. 3a-3c shows signal waveforms at various stages of the receiver circuitry.

FIG. 12 is a schematic of the pulse formation circuit.

FIG. 17 is a schematic of the input and output circuitry, microprocessor and data registers.

FIG. 19 is a schematic of the pulse frequency and pulse width circuits.

FIG. 20 is a schematic of the stimulation pulse frequency and pulse width control, current and voltage source controls, impedance measuring circuit and output switches.

DESCRIPTION OF THE PREFERRED EMBODIMENT

Figures 4, 5:
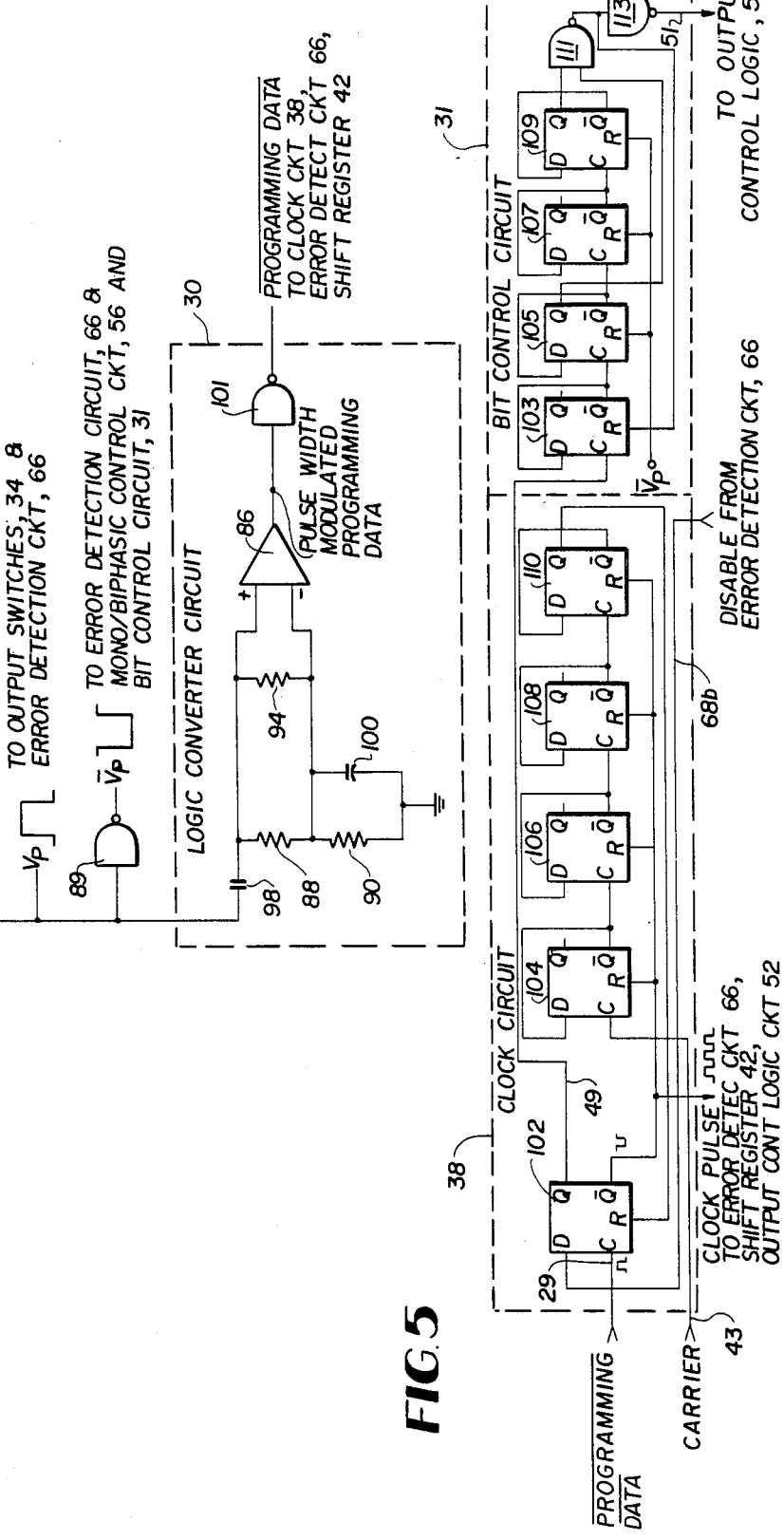
FIG. 4 shows a schematic diagram of the detector circuit, voltage storage circuit, and logic converter circuit of the receiver seen in FIG. 2.
FIG. 5 shows a schematic diagram of the clock circuit and the bit counter circuit of the receiver.

Referring now to the drawings, specifically FIG. 1, a simplified block diagram of the overall system is provided. The system includes a transmitter 10 and a receiver 12, the latter being surgically implanted beneath the patient's skin 13. The output of the receiver 12 is coupled via a plurality of lead wires 16a-16d to a plurality of electrodes 18a-18d. In the preferred embodiment of the invention, four leads are utilized, however, any convenient number of electrodes may be implanted as desired. For prosthesis, thousands of electrodes may be needed. Electrodes 18 are implanted adjacent the tissue to be stimulated, for example, nerve or muscle tissue. The receiver 12 may be manufactured by thick or thin-film hybrid technology or on a single integrated circuit using state-of-the-art techniques.

The transmitter 10 of the present invention includes programming controls (not shown) as well as transmitting circuits. In operation, the attending physician is required to select the specific pulse parameters that he desires for a specific patient. Through the programming controls, programming data is generated as a function of the physician's selection. This data generally includes control information defining which of the electrodes 18 are to be stimulated, as well as the electrical polarity of these electrodes relative to one another. It is an important feature of the present invention that each of the electrodes 18 is capable of assuming a programmed positive, negative or open-circuit status with respect to the other electrodes. Using the programming controls, the physician can modify the electrical configuration of the electrodes 18 to obtain the best response possible for the patient. If the selected electrodes fail to produce the desired response, the physician need only reprogram the transmitter 10 and transmit the new programming data.

The transmitter 10 includes a source of sinusoidal energy which functions as a carrier signal. In the preferred embodiment of the invention, the programming data is a pulse width modulated signal which is amplitude modulated onto the carrier signal by a modulation circuit. It should be recognized that although a pulse-width modulated signal is specifically discussed, any other type of digital, magnetic, or analog signal capable of defining the programming data may be utilized. The carrier is pulsed on and off as a "burst" signal to form the stimulation pulses which are transmitted by the transmitter 10 to the receiver 12. The parameters of the burst, such as amplitude, frequency and width, are preferably selected by the attending physician through the programming controls such that the resulting stimulation pulse signal can have different waveshapes. Also, the electrode impedance at specific frequencies and locations can be used to help determine which electrodes give the best response. This flexibility allows the physician to further control the stimulation response.

As will be explained with respect to FIGS. 10 plus, electrode impedance can be used with internal or external microprocessors which would automatically sequence through a number of programs to combine the impedance measurements with sensor measurements to determine which electrodes have the best response. The microprocessor can continuously monitor the impedance or perform the processing on a scheduled basis.

Note that although the transmitter 10 is shown in FIG. 1 as located external to the patient, it should be recognized that this placement is not meant to be limiting. The transmitter may also be implanted in the patient and be reprogrammed by measured internal physiological variables and/or a combination of external programming, measured variables and specific preprogrammed stored parameters. It may also be desirable to have the transmitter and receiver formed as an integral unit using internal and/or external power and programming sources. The integral unit will be described in reference to FIG. 16 after the description of the external transmitter.

Figure 10:
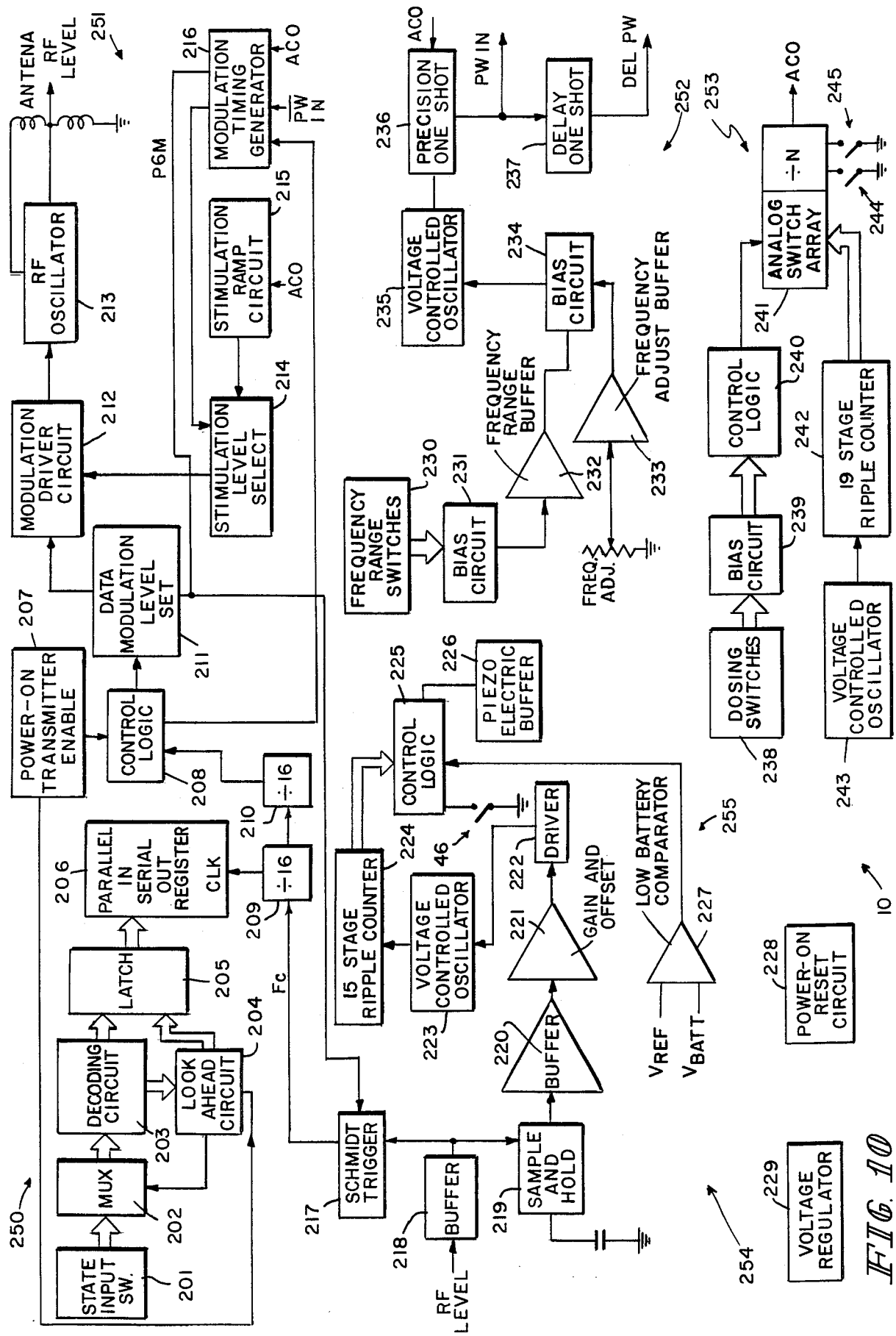
FIG. 10 is a block diagram of a transmitter incoporating the principles of the present invention.

Turning now to FIG. 10, a block diagram of the transmitter 10 is shown. The transmitter 10 includes an electrode selection circuitry 250, a transmitter circuit 251, a carrier signal definition circuit 252, a dosing circuit 253, a receiver antenna locator 254 and a low battery circuit 255. As will be described in more detail below, the electrode selection circuit 250 provides the necessary data for the selection of which electrodes will be used, the polarity of each of the electrodes to be used and whether it will be operated in mono or biphasic. This information is provided to the transmitting section 251 which also receives the amplitude and pulse width of the stimulation pulse from the stimulation definition circuit 252. The electrode selection or programming data are piggybacked or modulate the carrier which is the stimulation pulse. The dosing circuit 253 controls the operation of the transmitter circuit 251 to turn it on and off so as to provide dosing or the amount of time at which the stimulation pulses are to be applied. The receiver antenna locator circuit 254 provides an indication when the transmitting antenna circuit 251 is juxtaposed to the receiver antenna which is implanted. The low battery comparator circuit 255 provides an indication of when the power source of the transmitter is low using the same indicator as the antenna locator.

Figure 11A:
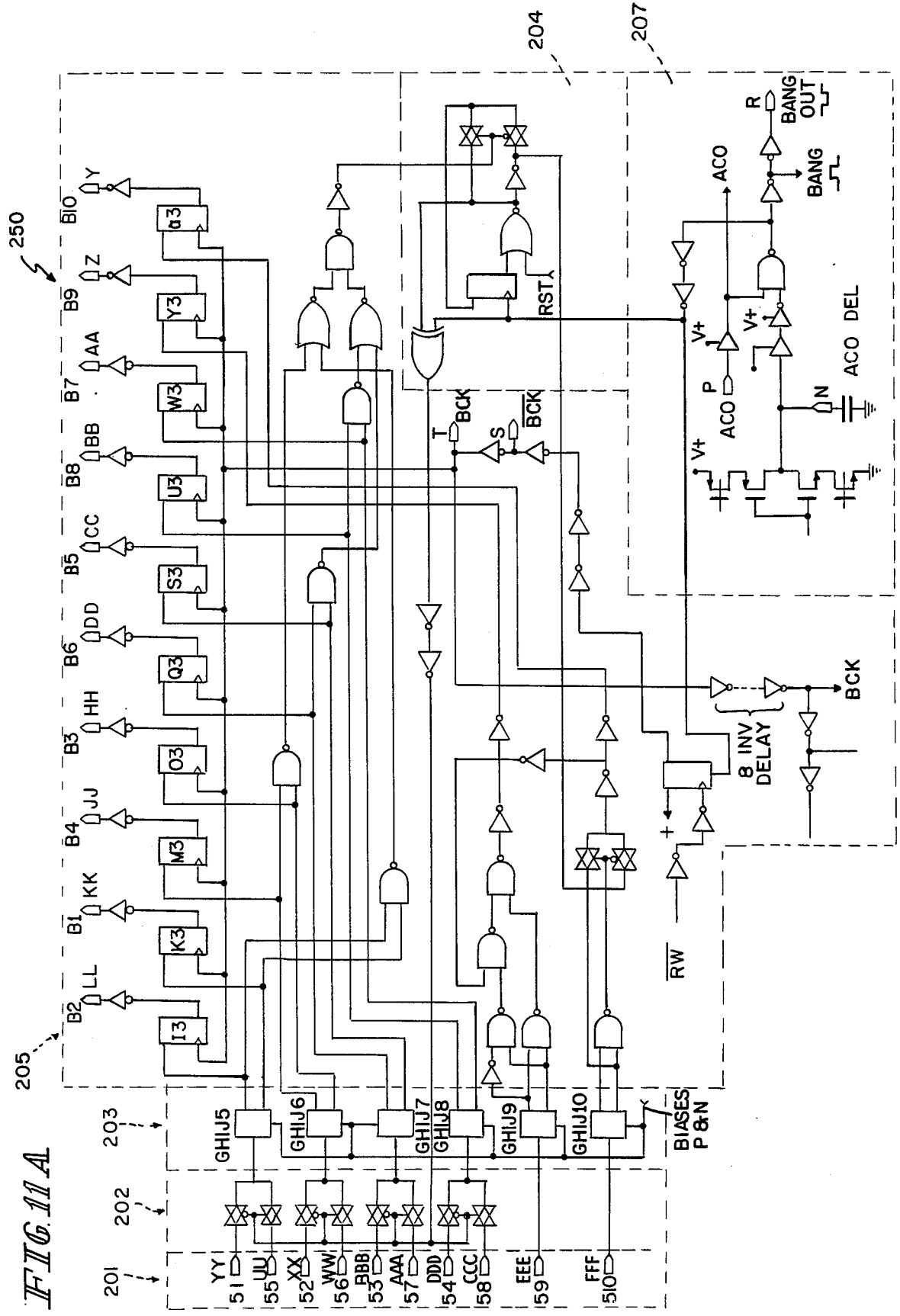
FIG. 11A and B is a schematic of the electrode selector programming data circuit.
Figure 11B:
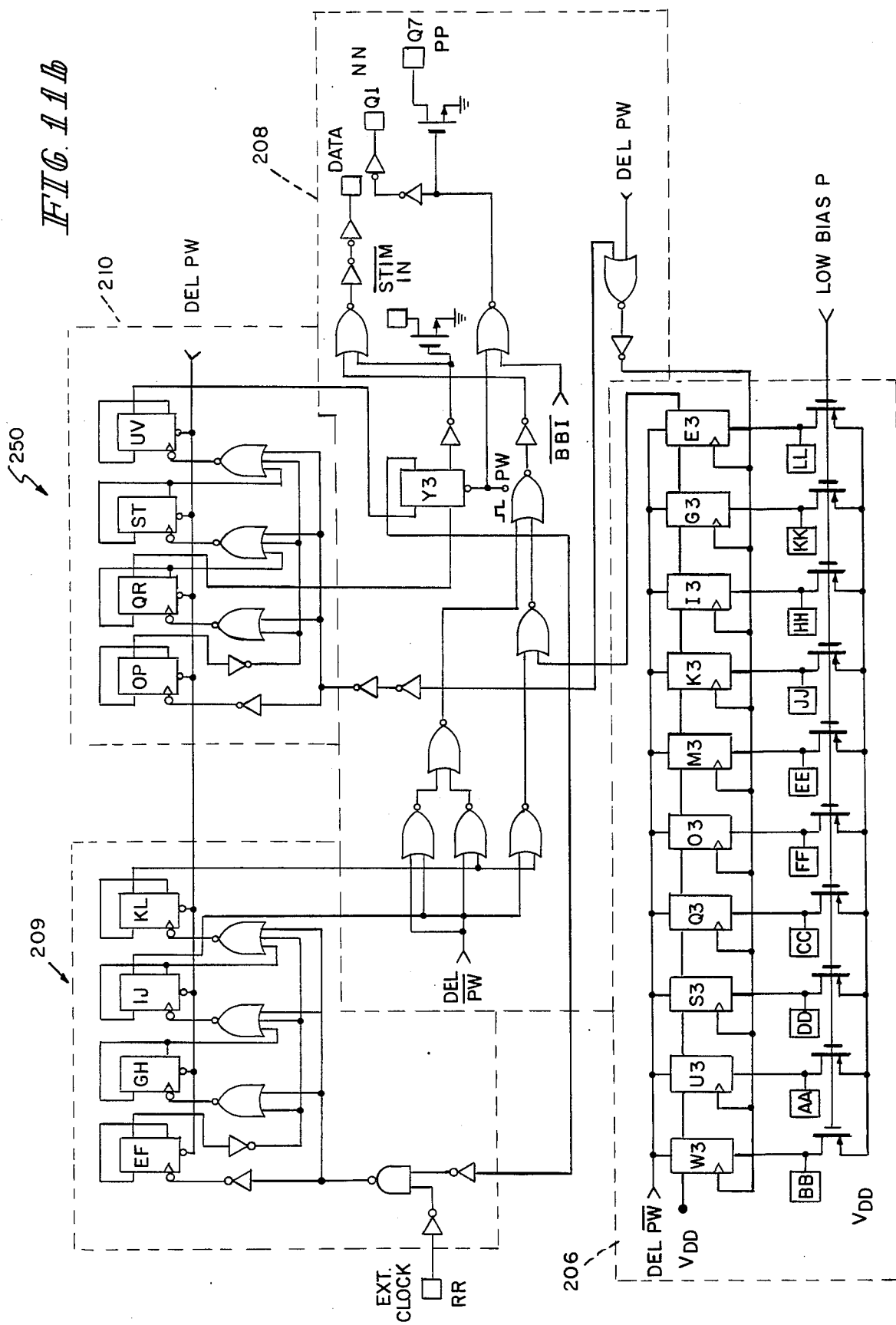

The detailed schematic of the electrode selection are programming circuit 250 as specifically illustrated in FIG. 11A.

Ten tri-state switches 201 allow programming of up to eight electrodes. Each electrode can be selected as an anode, cathode, or off, namely high impedance state.

Switches 1-4 are used to select a set of four electrodes of Channel A, and switches 5-8 can be used to program a second set of four electrodes of channel B or to alternatively program the first set of four electrodes. Switch 9 controls whether the stimulation is biphasic-consisting of alternating positive and negative pulses, or monophasic. Switch 10 allows the selection of either channel A set electrodes or Channel B set of electrodes.

Each switch 201 is connected to a decoding circuit 3 by an internal biasing circuit multiplexer 202. The decoding circuit 203 generates two bits which represent the three possible states of switches 1-8. Switches 9 and 10 are represented by one bit each. There are a total of 10 data bits, two for each of the four switches defining electrode state and one each from switches 9 and 10.

ON initial power up at the unit, whatever data is on the tri-state switches 201 will be held in latch 205. The look ahead circuit 204 toggles bit 10 if switch 10 is left in the off state. If switches 1-4 are selected, bit 10=1, and bit=0 if only switches 5-8 are selected.

The 10 bits are loaded into the parallel in-serial out register 206 before the first stimulation pulse and are clocked out serially. The clock signal is generated by a divide by 16 counter 209 which divides the 2MHZ $F_c$ signal received from the transmitter antenna via Schmitt trigger 27.

The 10 data bits are clocked serially out of 206 and are coded into pulse width modulated intervals for transmission by logic control circuitry 208, data modulation level set 211 and modulation driver 212.

The 10 bit serial code is shifted out at 206 into the data modulation level set circuit 211 which is offset from ground by the ratio of two resistors as shown in FIG. 12. This allows for setting the percentage of modulation on the RF oscillator to maintain stable operation.

After the 10 data bits are clocked into the control logic 208, a stimulation pulse STIM IN is generated by the second divide by 16 circuit 210 and control logic 208. The output of divide by 16 circuit 210 disables the data output of control logic 208 and the STIM IN pulse is input to modulation timing generator 216 of FIG. 12.

Figure 13:
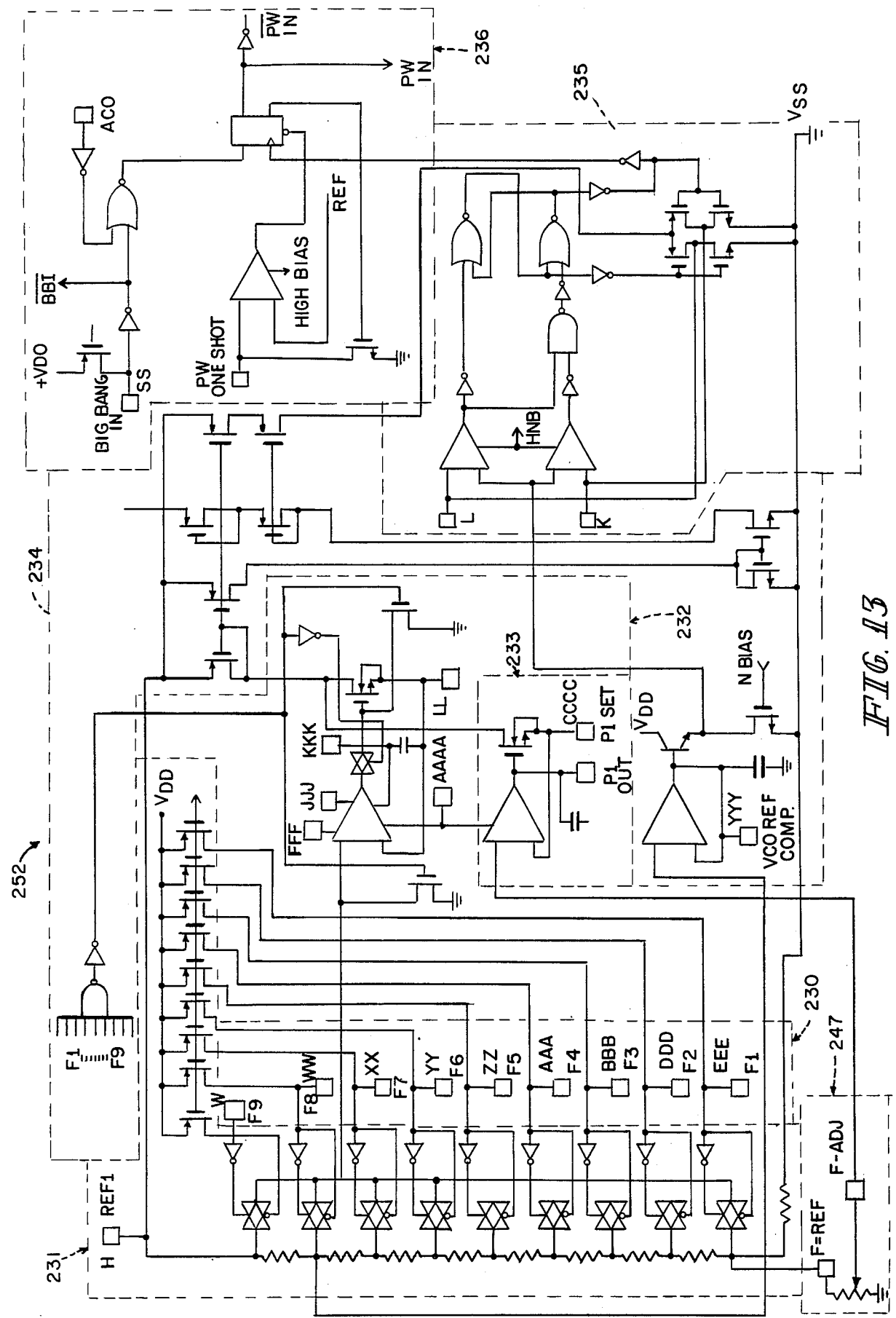
FIG. 13 is a schematic of the pulse frequency and width control circuit.

The frequency at which stimulation pulses are delivered can be controlled by both the frequency range switches 230 and the Frequency Adjust potentiometer 247 of FIG. 13. The switches 230 allow selection of 10 discrete frequency ranges, each separated by 150 pulses per second. The lowest range is from 0 to 150 HZ. The second from 150 to 300 HZ, etc. up to a maximum of 1500 HZ. The frequency within each range can be finely adjusted by the Frequency Adjust potentiometer 247.

The frequency switches 230 are each connected to analog switches and a resistor divider network 231 which establishes a discrete voltage level for each frequency range. This voltage is buffered by 232. The voltage generated by 247 is buffered by 233 and the bias circuit 234 forms a sum of the voltages which drives a voltage controlled oscillator 235.

The output from the VCO 235 is connected to a Precision one shot 236 to generate a pulse of adjustable duration for each falling/rising edge of the VCO output. This pulse is then delayed by the Delay one shot 237. The delayed pulse is generated to allow the RF oscillator 231 to begin oscillation approximately 10 microseconds before the data is shifted serially into the modulation driver 212.

The actual stimulation pulse width is generated after the 10th data bit has been shifted out of register 206 and before the end of the pulse generated by delay one shot 237. The range of stimulation pulse widths is nominally 25 to 1,000 microseconds.

The Precision one shot 236 includes logic responsive to an ACO signal generated by the dosing circuit 253 to disable the Precision one shot 236 and prevent generation of the signals PWIN and DELPW.

The amplitude of the stimulation pulse delivered by the receiver is proportional to the peak to peak value of the RF signal received during the stimulation portion of the waveform. The period is generated by the program and PW signals using logic circuitry in Modulation Timing Generator 216. The amplitude of the RF signal during the STIM interval is controlled by the stimulation level select circuit 214 and stimulation ramp circuit 215, via modulation driver 212 as illustrated in FIG. 12. A varying DC voltage is available by adjusting a potentiometer in the stimulation level select circuit 214. During the STIM interval, an analog switch is closed which connects this voltage to the Modulation driver circuit 212. This causes the RF oscillator 213 to operate at a fixed amplitide during the STIM interval.

The stimulation ramp circuit 215 is enabled when the Dosing switches 238 are selected. The output ACO of the Dosing circuit 253 turns an analog switch on and off which causes a capacitor to charge, increasing the stimulation voltage from 0 to the set value. Note that a variety of circuits could be inserted in place of this capacitor allowing triangle, exponential, pulse burst and other stimulator waveforms.

Figure 14:
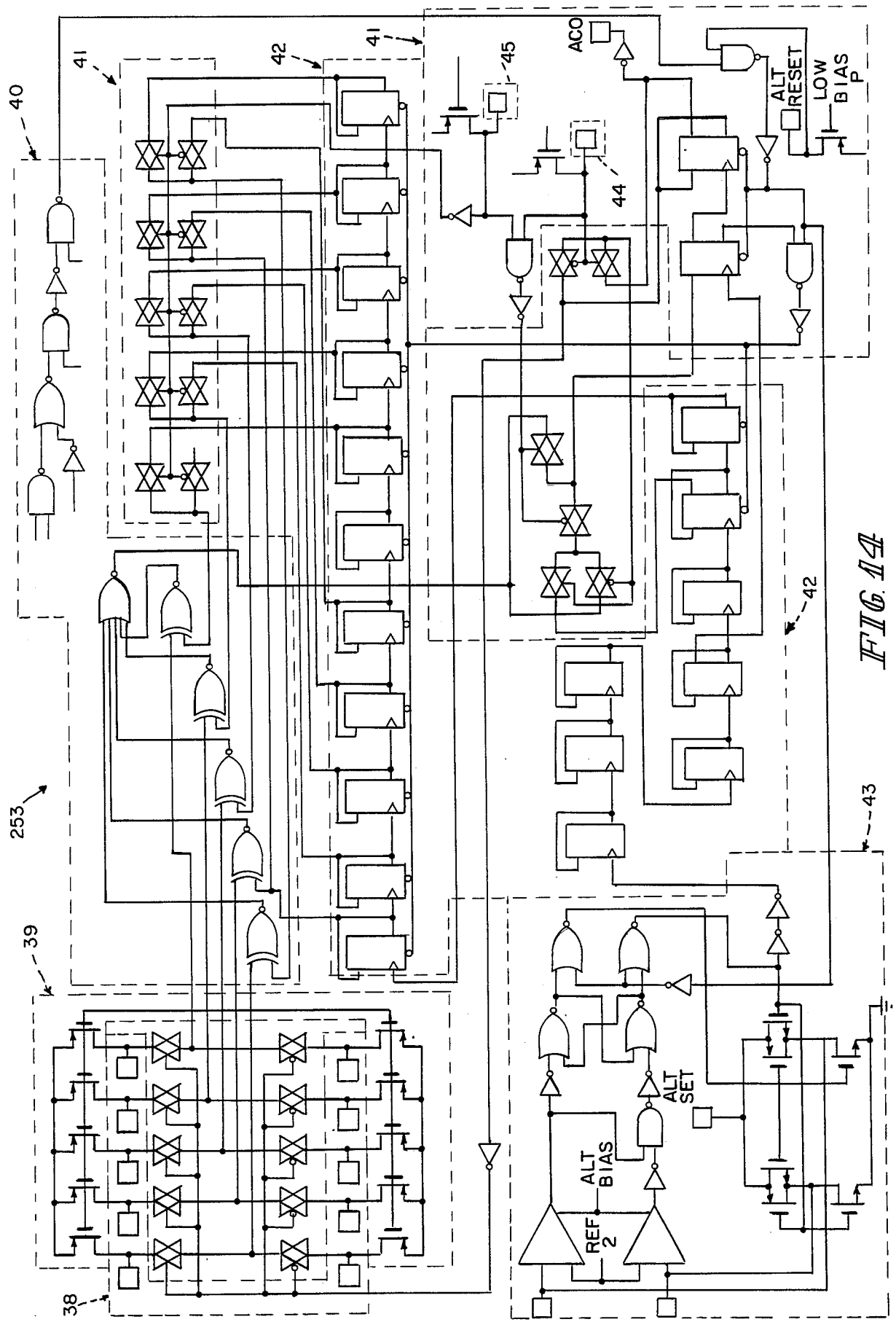
FIG. 14 is a schematic of the Dosing circuit.

The transmitter is provided with a Dosing (automatic turn on and turn off) feature 253 illustrated in FIG. 14 as 253. The ON and OFF times are controlled by the Dosing switches 238 and switches 244 and 245.

With Switches 244 and 245 in the open circuit position, Dosing work as follows:

There are five dosing switches for OFF time and five dosing switches for ON time. These time intervals are selectable from 30 seconds to 15.5 minutes in 30 seconds intervals or may be any multiple of these times.

Each switch is connected to an internal bias circuit which includes an analog switch. The switch combination represented by the control logic circuit 240, control analog switches 241 which select what stages of a 19 stage ripple counter 242 are to be selected as outputs. The ripple counter 242 is clocked by a Voltage Controlled Oscillator 243 and it provides 19 stages of binary division. The output signal is called ACO OUT for Alternate Channel Oscillator.

The ACO OUT is tied to Precision one shot 236 and to Modulation timing generator 216 and disables the PW signal, which disables STIM and PGM allowing no output.

When the ACO signal toggles, high, it enables the Stimulation Ramp circuit 215 providing a slow turn on of stimulation.

Three other modes are possible through selection of switches 44 and 45. Activating either switch changes the ripple counter 242 length for the long and/or short time periods, such that an additional division of 64 is performed on the ACO clock VCO 243. This feature is used when a fixed short off and an adjustable long ON period (or vice versa) or two fixed short periods are required, as in use of the transmitter with an 8 channel, 2 receiver system, and/or a multiplexed 4 channel system.

It should be noted that although ten dosing switches and a 19 stage ripple counter are disclosed, any number of switches and/or counter stages could be incorporated to increase or reduce the control capability and anytime intervals may be used.

The unit has a feature which allows the exact placement of the transmitting antenna above the implanted receiver. The unit provides an audible tone generated by a piezoelectric buzzer 226 which increases in frequency and pitch as the antenna nears the implanted receiver. The audible tone turns off automatically after several seconds.

Figure 15:
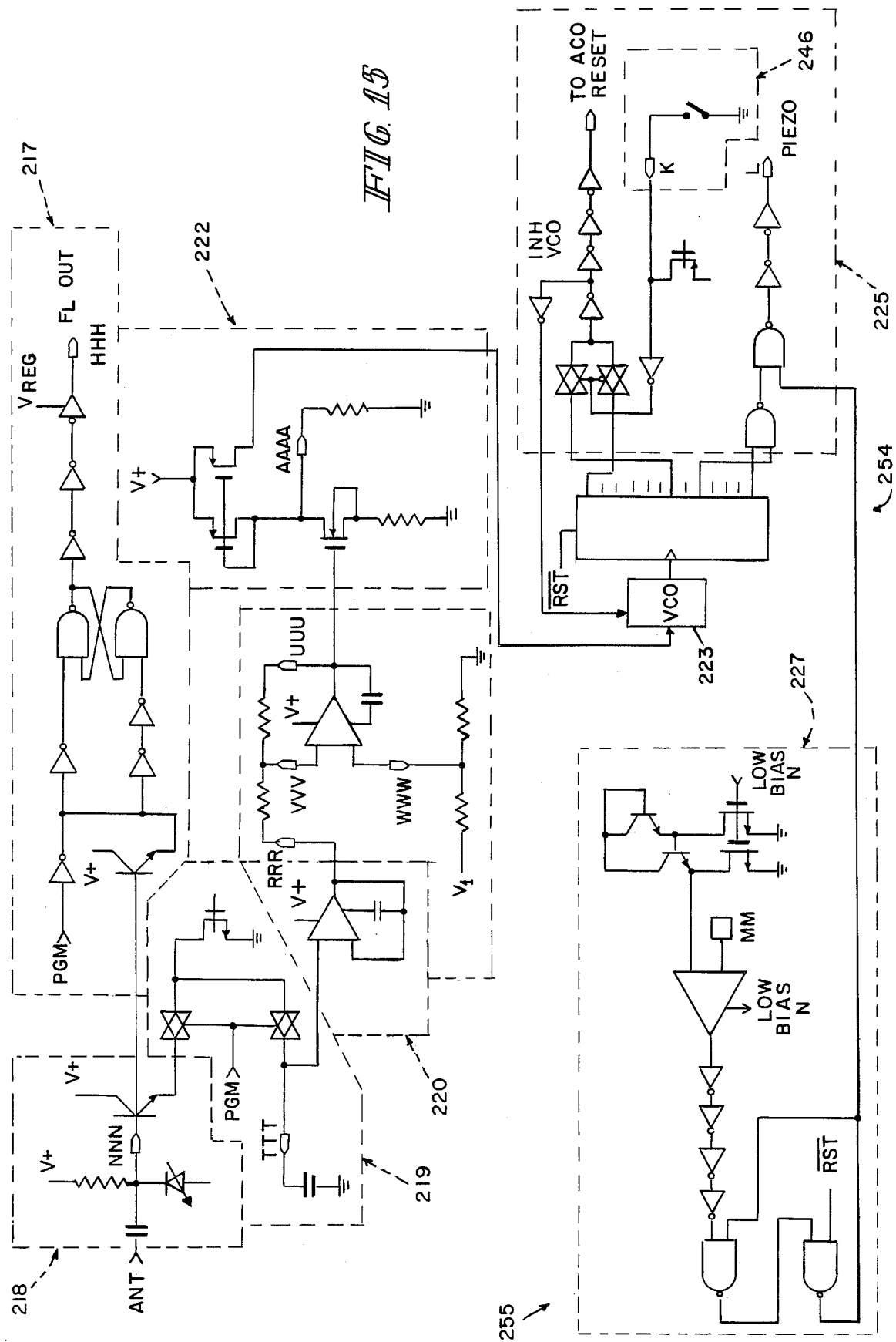
FIG. 15 is a schematic of the Antenna locator and low battery circuits.

The circuit 254, illustrated in FIGS. 10 and 15, operates as follows. When the antenna is distant from the receiver, there is no coupling between the two antennas, which act as a transformer. With no coupling, the amplitude of the RF signal generated by the RF oscillator 213 is maximum. When the antenna of the transmitter is brought near the receiver, the coupling increases, which loads the antenna of the transmitter, lowering the RF signal. The signal labelled RF Level is used to monitor this action.

RF Level is connected to a buffer 218 and the output of this buffer is connected to both a Schmitt trigger 217 and a Sample and Hold circuit 219. The output of the Schmitt trigger 217 is labelled $F_c$ out and is used as the main clock signal for data transmission. A capacitor in the Sample and Hold circuit is charged by connecting it to the output of buffer 218 via an analog switch 219. The voltage across the capacitor is buffered by a unity gain buffer 220 and used as the input to an inverting amplifier with gain and adjustable offset 221. The offset can be used to null the output of 221 when the RF level is at a minimum. As the RF level increases, the charge on the capacitor rises, and the output of 221 decreases. This provides less drive voltage for the Driver 222 which controls a Voltage controlled oscillator 223. Less drive causes the frequency of the VCO 223 to increase. The output of the VCO 223 is connected as the clock input of a 15 stage ripple counter 224. The $Q_0$ and the $Q_8$ output of the counter are NANDED together and that output drives a piezoelectric buzzer 226. When the $Q_{15}$ output of the ripple counter 224 goes high, it inhibits the VCO 223, which is the automatic turn off feature.

Switch 246 enables this feature. If put into the disable position, the $Q_{10}$ output at the ripple counter 224 inhibits the VCO 223. The inhibit signal is selected by the Control logic circuit 225.

A low battery circuit 255 provides an audible signal to determine the battery status. The battery voltage is divided by a resistor divider in the Low Battery Comparator circuit 227. This voltage is compared to an internally generated reference voltage. When the $V_{BATT}$ voltage goes below the internal reference, the comparator 227 changes state. This signal is connected to the control logic circuit 225 and inhibits the signal driving the piezoelectric buzzer 226. If the unit is turned on and no audible tone is heard, that means the battery needs to be replaced.

Alternately, the signal from the low battery comparator 227 may be connected to AC 10 which would inhibit operation of the transmitter automatically when $V_{BATT}$ dropped below the reference level.

Turning now to FIG. 2, a block diagram of the receiver 12 is shown. This device includes an antenna 20 coupled to a detector circuit 22 which provides envelope detection of the transmitted signal to remove the carrier signal. With reference to FIG. 3a, the transmitted burst is shown comprising the carrier signal 26 which includes the pulse width modulated programming data riding as a ripple. The output of the detector circuit 22 is seen in FIG. 3b as an envelope of the transmitted burst with the carrier removed, and includes the transmitted pulse $V_p$ and the programming data 28 modulated thereon. It should be noted that the transmitted pulse $V_p$ includes the stimulation pulse $V_s$ as seen in FIG. 3b. In particular, the stimulation pulse $V_s$ is that portion of the transmitted pulse $V_p$ which doesn't include the programming data sequence. In the preferred embodiment of the invention, the programming data 28 is modulated on the first half of the transmitted pulse $V_p$. Therefore, the second half of the transmitted pulse $V_p$ is used as the stimulation pulse $V_s$.

The output of the detector circuit 22 is connected to a logic converter circuit 30 which decodes the programming data 28 from the transmitted pulse $V_p$. The transmitted pulse $V_p$ which includes the stimulation pulse $V_s$, is routed via conductor 32 to the output switches 34 connected to the electrodes 18. The steady state or long-term energy derived from the received pulses is stored in a voltage storage circuit 36 as a voltage signal Vm. The decay time of the voltage signal Vm is much longer as compared with the time between reception of the transmitted bursts, and therefore this voltage is used to power the receiver circuitry between the reception period. This feature also allows for continued system operation during those brief periods when the receiver might lose the transmitted signal due to dislocation of the antenna 20 during routine activities of daily living.

It should be noted that a small, internal power source could be incorporated into the receiver to augment or replace the voltage storage circuit 36. Such an internal power source serves to convert the receiver memory, to be described below, into a non-volatile memory.

Figure 25:
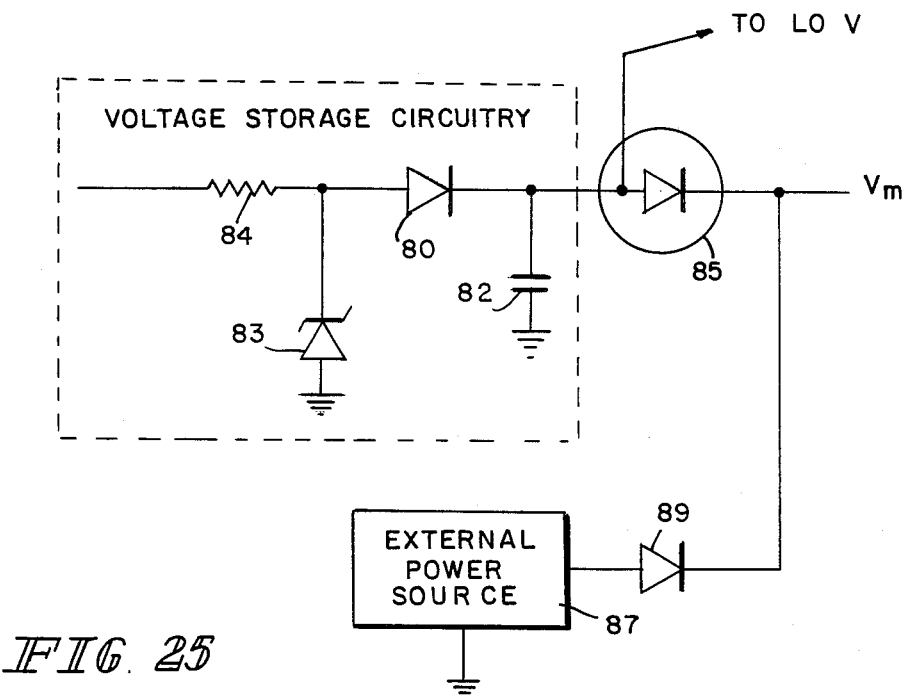
FIG. 25 is a modification of FIG. 4 to provide an internal power source.

FIG. 25 illustrates the added circuitry required to provide an internal power source to FIG. 4. It simply consists of a diode 85 isolating the capacitor 82 from the internal power source 87 and a diode 89. The internal power source might consist of a battery, fuel cell, bioauto fuel cell, heat/electricity source, glucose/electricity source etc., or any other implantable power means which might be developed. The power source 87 remains inactive so long as the circuitry receives transmitted RF from the coil to reverse bias diode 89. If the RF should go below a specified level or the signal repetition rate goes below the level required to keep capacitor 82 charged to a voltage greater than Vm minus two times the diode drops, then the internal power source would automatically bias on diode 89 and provide power to the memory in the implant. This type of switching is well known in the industry and provides for an uninterruptable power source.

An additional change in the circuitry would be that the loss of voltage comparator input presently called Vm would be moved in front of the diode 85 and provided as signal LOV (Loss of Voltage). With this connection the LOV comparator would still reset in order to allow reprogramming if the transmitter was off for enough time to let the capacitor charge below that level although the internal voltage source would store the program in the memory.

Additional circuitry would be anticipated to require bit ten and/or bit nine (or additional program bits) to be in some predetermined state (they would act as a parity bits). These bits would preclude latching in new programming data unless the predetermined states were transmitted in the new programming data (unit would not return to programming mode unless the proper code was transmitted—presently LOV would reset to programming mode).

In operation, the battery or other internal power means 87 would provide a way to ensure that the receiver remains programmed even though minute movements in normal activities of daily living might move the antenna away from the receiver and therefore lose program area. This would potentially improve the reliability of the RF link and might also allow the program data to only be transmitted for initial programming, thereby reducing the overall power consumption of the external transmitter and improving battery life. In order to fully utilize the idea of not transmitting program data except initially, it would be desirable to use the same additional data bit and/or bit 9 or 10 as predetermined codes (as above) in order to automatically change the normal requirements of the 10 bit counter. In the embodiment of FIG. 2, it required 10 data bits prior to turning on the outputs to deliver stimulation. The exact change would relate to bit counter circuit 31 and logic would be provided to tie line 51 to the output control logic circuit 52 to a high state. Therefore the circuit would no longer delay application of Vp to the electrodes and stimulation would be delivered during the entire transmitted burst.

Thus, once the receiver is programmed, stimulation can be achieved by transmitting stimulation pulses without the programming data. In practice, the physician will program the receiver at the hospital using a sophisticated transmitter. The patient would then require only a simple transmitter at home which could provide the stimulation pulses.

The output of the logic converter circuit 30 is seen in FIG. 3c and consists of the pulse-width modulated programming data 28 defining which of the electrodes 18 are to be stimulated, the electrical polarity of these electrodes relative to each other, whether the electrodes will be stimulated in the mono or biphasic mode, and which of two redundant receivers or channels (if two are used) are to be activated. The monophasic mode is one wherein the polarity of the stimulated electrodes is kept constant. In the biphasic mode, the relative polarity of the stimulated electrodes reverses with each stimulation cycle. The programming data 28 is applied to input 29 of a clock circuit 38 which forms clock pulses 39 for the rest of the receiver circuitry. These clock pulses, which are seen in FIG. 3d, have a duty cycle which is a function of the carrier frequency, the carrier signal being applied to the clock circuit via conductor 43. The programming data 28 is further applied via conductor 40 to the data input of a memory comprising a serial-in, parallel-out shift register 42. This data 28 is clocked into the data input of the shift register by the clock pulses 39 produced by the clock circuit 38 and delivered to the clock input of the shift register via conductor 44. The data input to the shift register is seen in FIG. 3e.

The shift register 42 includes a first output data bus 50 for connecting a portion of the programming data 28 to an output control logic circuit 52. This portion of the programming data determines which electrodes will be stimulated and the relative positive or negative polarity of these electrodes. The output control logic circuit 52 drives the plurality of output switches 34 to route the stimulation pulses $V_s$ from conductor 32 to the appropriate electrodes 18 defined in the programming data 28.

The shift register 42 includes a second output data bus 54 which connects a second portion of the programming data 28 to a mono/biphasic control circuit 56. This circuit allows the physician to program for stimulation pulses of alternating polarity. As stated above, in the monophasic mode, the relative polarity of the stimulated electrodes remains constant; however, in the biphasic mode, this polarity reverses on each stimulation cycle. This feature is selected during programming by the programming controls and is transmitted as a portion of the programming data 28. The output of the mono/biphasic control circuit 56 is connected to the output control logic circuit 52 via conductor bus 57 such that the mono or biphasic parameter can be used to control the stimulation pulses applied to the electrodes.

A third output data bus 58 of the shift register 42 connects a final portion of the programming data 28 to a channel enable logic circuit 60. This circuit is incorporated to allow for the possibility of adding a second receiver. In particular, the channel enable programming data, also programmed by the physician, may specify which of two redundant circuits in the same receiver package, A or B, is to be activated by the stimulation pulses. This feature is desirable should one receiver become defective or a second receiver be required to stimulate another group of electrodes in a separate region of the patient's body. More importantly, the output of the channel enable logic circuit 60 also controls the routing of the programming data 28 through the output control logic circuit 52. In particular, when the channel enable logic circuit is activated, as would only occur when (a) the appropriate channel A or B has been selected, (b) a predetermined number of consecutive, identical programming data sequences have been received, and (c) no invalid electrode combinations which would short the receiver have been selected, a pulse on conductor 63 is transmitted to output control logic circuit 52. This signal, in combination with the output of bit control circuit 31, to be described below, is used to control the application of the stimulation pulses $V_s$ to the output switches 34. Note that if an invalid combination is selected, a disable signal is outputted from the output control logic circuit 52 on conductor 64.

The pulse-width modulated programming data 28 is also applied to one input 65 of an error detection circuit 66 via conductor 46. The other input 67 of the error detection circuit is provided by the serial output 69 of the last bit of the shift register 42 over conductor 47. The clock pulses 39 are also applied via conductor 45. When the error detection circuit determines that a predetermined number of consecutive, identical sequences of programming data have been received, an output enable signal is provided via conductor 68a to enable the channel enable logic circuit 60. In the preferred embodiment, four consecutive, identical sequences are required. A bit counter circuit 31 shown in FIG. 2 receives a signal over conductor 49 from clock circuit 38. The bit counter is a ÷10 flipflop configuration commonly known in the art. The output of this circuit is used to control the output control logic such that the output switches cannot be turned on until the ten data bits of the programming data sequence have been received. This circuit thus forms delay means for delaying application of $V_p$ to the electrodes. Therefore, only the stimulation pulse $V_s$ of $V_p$ will be applied to the output switches. As descirbed above, the channel enable logic circuit 60 and the bit counter circuit 31 control the output control logic circuit 52 and the output switches 34 to deliver the energy of the stimulation pulses $V_s$ to the electrodes 18 defined in the programming data 28. During stimulation, the output enable signal from the error detection circuit 66 functions to turn the clock circuit 38 off via conductor 68b. The programming data, however, remains in the shift register 42 until the voltage Vm decays to a predetermined value, such as will occur when the transmitter is turned off or the antenna 20 is decoupled from the receiver. Thus, once four consecutive, identical programming data sequences are received and the channel enable logic circuit 60 is enabled, the subsequently-received stimulation pulses are applied to the electrodes without further programming after the bit counter circuit 31 times out.

Finally, a loss of voltage comparator circuit 70 is provided to detect when the voltage Vm in the voltage storage 36 decays below a predetermined value. Specifically, the circuit receives the voltage Vm stored in the voltage storage circuit 36 at one input 71 and compares this value with a predetermined internally set reference voltage Vref received at its second input 73. Should the voltage Vm be less than the reference voltage as would occur if the transmitter is turned off or the stimulation pulses are not being received properly, an output signal on conductor 72 resets the error detection circuit 66, which disables the channel enable logic circuit 60. Once the channel enable logic circuit 60 has been disabled, four consecutive, identical programming data sequences must be received before the receiver can provide stimulation.

Summarizing, when the transmitter is turned on, the receiver logic will look for four consecutive, identical sequences of programming pulses. This part of the receiver operation defines a programming mode. Once these sequences are received, the error detection circuit 66 and the channel enable logic circuit 60 lock in and route the stimulation signal to the output switches to deliver the energy of the stimulation pulses to the electrodes after the bit counter circuit times out for each burst. This part of the receiver operation defines a stimulation mode. If the programming data fails to produce a desired physical response, the physician can reprogram the transmitter to form a new sequence of programming data, this sequence defining a different polarity or mono/biphasic capability, or a different combination of electrodes. Before reprogramming, the receiver must be disabled by turning off the transmitter or decoupling the antenna 20 such that the loss of voltage comparator circuit 70 resets the error detection circuit 66. When this occurs, the circuit can re-enter the programming mode. Alternatively, the receiver could monitor the programming signal continuously so that any change in programming would alter the contents of the receiver memory.

With reference to FIG. 4, the detector circuit 22, voltage storage circuit 36, and logic converter circuit 30, are shown in detail. More specifically, the transmitted stimulation pulses are inductively coupled transcutaneously to the receiver by inductor 74. Diode rectifiers 76 and 77 are connected to the inductor 74 to rectify the received signal. Capacitors 78 and 79 are chosen to respond only to envelope variations in the rectified signal so as to filter out the carrier signal 26 and provide a proper ground reference for the rectified signal.

The output of the detector circuit 22 is stored as voltage Vm in the voltage storage circuit 36 which comprises diode 80, capacitor 82, optional zener diode 83 and resistor 84. Alternatively, a rechargeable voltage source could be substituted for capacitor 82. The short-term output of the detector circuit 22 is the transmitted pulse $V_p$ which includes the pulse-width modulated programming data 28 on its envelope as seen in FIG. 3b. The transmitted pulse Vp is applied to the logic converter circuit 30 which serves to decode the programming data 28 from the stimulation pulses Vs. The logic converter is well known in the art and comprises an operational amplifier 86, resistors 88, 90 and 94, and capacitors 98 and 100. Note that other configurations of the signal shaping passive components may also be used. The output of the logic converter 30 is inverted by the NAND gate 101 to form an inverted programming data signal which is applied to (a) the input 29 of the clock circuit 38 of FIG. 5; (b) the data input of the shift register 42 of FIG. 6; and (c) the input 65 of the error detection circuit 66 of FIG. 7. A NAND gate 89 is provided to form an inverted stimulation pulse $\overline{V}_p$.

The clock circuit 38 and bit counter circuit 31 are shown in detail in FIG. 5. The clock circuit consists of a control D-flip-flop 102 which includes a clock input 29, a data input, an inverted $\overline{Q}$ output, and a reset line. The rest of the clock circuit comprises four serially connected D flip-flops 104, 106, 108 and 110. These flip-flops are arranged as a divide by eight counter, with the clock input of the counter being derived from the carrier signal via conductor 43. The non-inverted Q output of the last flip-flop 110 of the counter is connected to the reset line of the control flip-flop 102. Also, the inverted $\overline{Q}$ output of the flip-flop 102 is connected to the reset lines of the counter flip-flops 104, 106, 108 and 110.

In operation, the pulse-width modulated programming data, which is inverted by NAND gate 101 of FIG. 4, is applied to the clock input 29 of the control flip-flop 102, so that the first falling edge in the signal will toggle the inverted $\overline{Q}$ output of this flip-flop to a logic low state. This signal resets the counter flip-flops 104, 106, 108 and 110 via their reset lines, such that the counter will start counting carrier pulses from zero. After eight cycles of the carrier-wave are counted, the non-inverted Q output of flip-flop 110 goes to logic high and resets the control flip-flop 102, terminating the pulse on its inverted $\overline{Q}$ output. The $\overline{Q}$ pulse from the control flip-flop 102 is the clock pulse 39 for the rest of the receiver circuit. It should be obvious to one skilled in the art that clock circuit 38 acts essentially as a monostable multivibrator, or one-shot circuit, with the pulse-width modulated data being used simply to trigger generation of the clock pulses at a frequency determined by the programming data and with a duty cycle determined by the carrier frequency.

The bit counter circuit 31 is also shown in FIG. 5. This circuit comprises D flip-flops 103, 105, 107, and 109 connected as a divide-by-ten counter, and NAND gates 111 and 113. The clock input to flip-flop 103 is provided by the non-inverted Q output of flip-flop 102 of the clock circuit 38. The inputs to NAND gate 111 are provided by the non-inverted Q outputs of flip-flops 105 and 109. Therefore, after ten bits of programming data have been received by the bit counter circuit 31, the output of NAND gate 111 goes logic low. This logic low signal is inverted by NAND gate 113 and applied to the output control logic circuit 52 via conductor 51 as will be described in detail below. The inverted transmitted pulse $\overline{V}_p$ is used to reset the counter via the reset inputs of of flip-flops 105, 107, and 109. Thus, the bit counter circuit is reset after each transmitted pulse.

Figure 6:
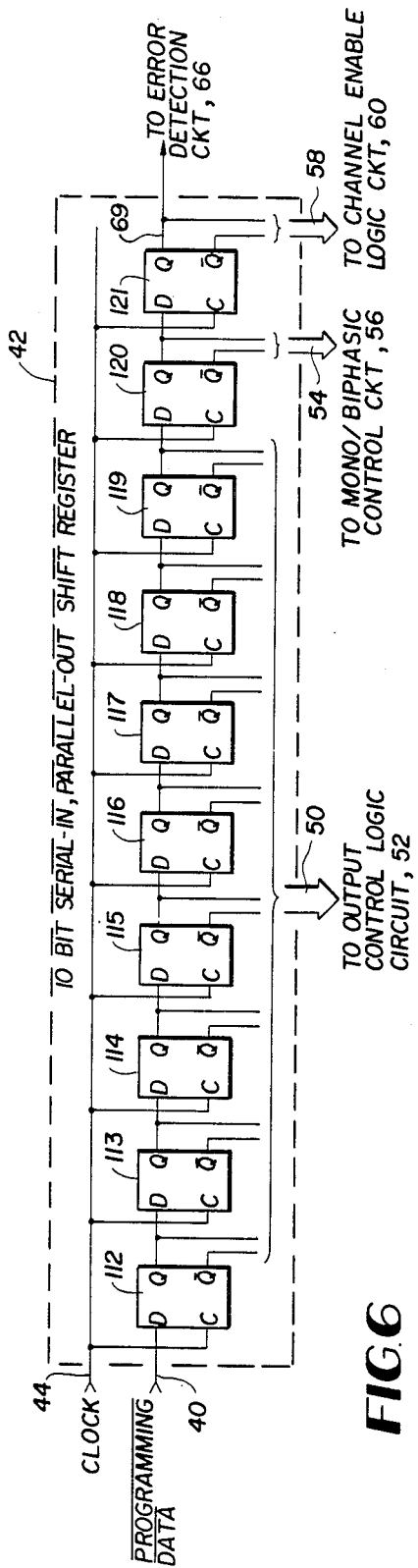
FIG. 6 shows a schematic diagram of the shift register of the receiver.

The shift register 42 of the receiver 12 is shown in FIG. 6, and comprises ten D-flip-flops 112–121 connected in a serial-in, parallel-out structure. In particular, the non-inverted Q output of the $n^{th}$ stage of the shift register 42 is connected to the data input of the succeeding or $n+1^{th}$ stage. The inverted programming data 28 is applied from NAND gate 101 of the logic converter circuit 30 in FIG. 4 to the data input of the first flip-flop 112 of the shift register 42 over conductor 40. The clock pulses 39 derived from the clock circuit 38 of FIG. 5 are applied to the clock inputs of each flip-flop 112–121 via conductor 44. The inverted $\overline{Q}$ and the non-inverted Q outputs of flip-flops 112–121 form the first output data bus 50 which connects a portion of the programming data 28 to the output control logic circuit 52 of FIG. 9. The non-inverted Q and inverted $\overline{Q}$ outputs of flip-flop 120 form the second output data bus 54 which connects a second portion of the programming data 28 to the mono/biphasic control circuit 56 of FIG. 8. Finally, the non-inverted Q and inverted $\overline{Q}$ outputs of flip-flop 121 form the third output data bus 58 for connecting the final bit of the shift register 42 to the channel enable logic circuit 60 of FIG. 8. Also, the non-inverted Q output 69 of the last flip-flop 121 is connected to the error detection circuit 66 of FIG. 7. The number of flip-flops in the shift register 42 is equal to the number of bits in the programming data sequence. Note that although ten bits are shown in the preferred embodiment, any number may be used such that other programmable parameters may be specified by the programming data. Also, it is envisioned that the shift register 42 comprises either volatile or non-volatile elements.

Figure 7:
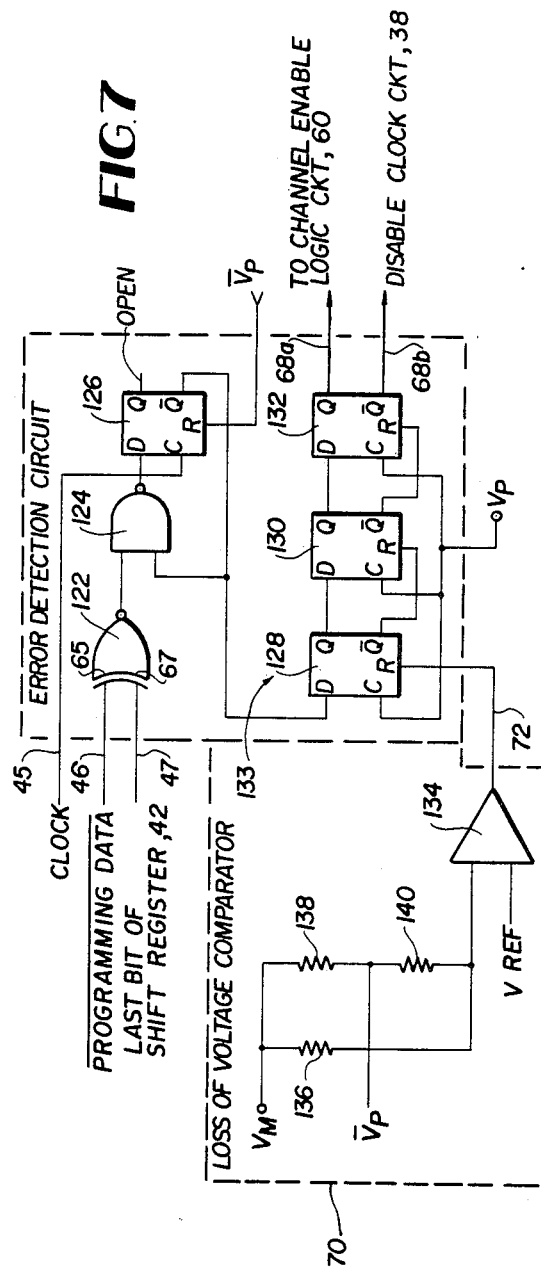
FIG. 7 shows a schematic diagram of the error detection circuit and the loss of voltage comparator circuit of the receiver.

The error detection circuit 66 is seen in FIG. 7 and comprises exclusive NOR (X-NOR) gate 122, NAND gate 124, and D flip-flops 126, 128, 130 and 132. The flip-flops 128, 130 and 132 define a three count ring counter 133. One of the inputs 65 of the X-NOR gate 122 is the inverted programming data 28 from NAND gate 101 of the logic converter in FIG. 4, while the other input 67 is provided by the non-inverted Q output 69 of the last flip-flop 121 of the shift register 42. The output of the X-NOR gate 122 is logic high if both of the inputs are high or both are low; otherwise, the output is low. Since the inputs to the X-NOR gate 122 are the input and output of the shift register 42, the output of the X-NOR gate 122 indicates whether the bits of the incoming programming data sequence match the bits of the previously-received programming data sequence. The output of the X-NOR gate 122 is connected as one input to the NAND gate 124, the output of which is connected to the data input of the flip-flop 126. The other input to the NAND gate 124 is provided by the inverted $\overline{Q}$ output of flip-flop 126. The clock pulses from clock circuit 38 of FIG. 5 are connected to the clock input of flip-flop 126. The inverted $\overline{Q}$ output of the flip-flop 126 is also connected to the data input of the ring counter 133. The non-inverted Q output of the last flip-flop 132 in the counter 133 is routed via conductor 68a to the channel enable logic circuit 60 of FIG. 7 and to the output control logic circuit 52 of FIG. 9 via conductor 68c. The inverted $\overline{Q}$ output of the flip-flop 132 is routed via conductor 68b to disable the clock circuit 38 by providing a logic low to the data input of the control flip-flop 102 in FIG. 5. Thus, a logic high on the inverted $\overline{Q}$ output of flip-flop 132 keeps the receiver in the programming mode and a logic low places the receiver in the stimulation mode. Finally, the reset line of flip-flop 126 is tied to the inverted transmitted pulse Vp provided by NAND gate 89 in FIG. 4, and the clock inputs of the flip-flops 128, 130 and 132 are tied to the non-inverted Vp signal.

FIG. 7 also shows the loss of voltage comparator circuit 70 which compares the energy Vm in the voltage storage circuit 36 of FIG. 4 to a predetermined voltage $V_{ref}$. In particular, the long-term voltage Vm is applied to one input of a comparator 134 via a resistor divider network 136, 138 and 140. The reference voltage, which is internally preset, is applied to the other input of the comparator 134. An output signal from the comparator 134 occurs whenever the voltage Vm is less than the predetermined reference voltage. As discussed above, this condition occurs when the receiver is no longer receiving stimulation pulses, or the pulses are not being received properly. The loss of voltage output is routed via conductor 72 to the reset line of the counter 133 in the error detection circuit. Thus, when a loss of voltage occurs, the error detection circuit is effectively reset and the receiver can re-enter the programming mode. Thereafter, four consecutive, identical programming data sequences must again be received before the receiver goes back into the simulation mode.

The operation of the error detection circuit 66 of FIG. 7 will now be explained in detail. The inverted pulse $\overline{V}_p$ resets flip-flop 126 for each transmitted burst received by the receiver. Therefore, the inverted $\overline{Q}$ output of flip-flop will be a logic high signal which is applied to NAND gate 124. As long as all the data bits of consecutively-received programming data sequences match, the output of X-NOR gate 122 will be logic high. Since both inputs of NAND gate 124 are logic high, its output is a logic low signal which is applied to the data input of flip-flop 126. Note that flip-flop 126 is clocked every bit of the programming data by the clock pulses 39 of FIG. 3d to keep the inverted $\overline{Q}$ output at logic high. If the inverted $\overline{Q}$ output of flip-flop 126 is logic high at the end of the stimulation pulse, this logic high signal is applied to the data input of the counter 133, indicating that consecutively-received programming data sequences are identical. After three identical sequences are consecutively-received and found to be identical with the initial sequence received, the ring counter 133 will provide a logic high output from the non-inverted Q output of flip-flop 132. This output is coupled via conductor 68a to the channel enable logic circuit 60 and indicates that the receiver may enter the stimulation mode. The inverted $\overline{Q}$ output of flip-flop 132 goes to logic low during the stimulation mode to disable the clock circuit 38 of FIG. 5 via the conductor 68b. It may also be used to disable to other parts of the receiver once the unit is programmed.

If any of the bits in the incoming programming data, however, do not match the bits in the previously-received programming data sequence, the output of X-NOR gate 122 is logic low and therefore the output of NAND gate 124 is logic high. This logic high signal causes the inverted $\overline{Q}$ output of flip-flop 126 to go to logic low, and thus NAND gate 124 will continue to provide a logic high output until the incoming data bits match the previously received data bits. In addition, a loss of voltage signal on conductor 72 may also be applied to reset the counter 133, such that the receiver can re-enter the programming mode after a loss of voltage.

Figure 8:
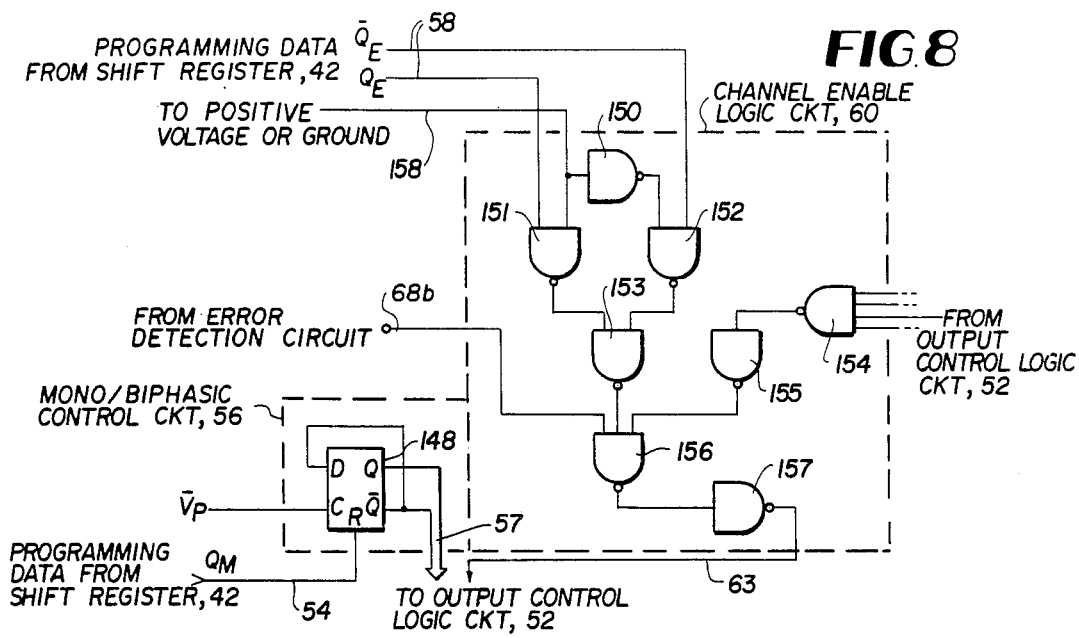
FIG. 8 shows a schematic diagram of the channel enable logic circuit and the mono/biphasic control circuit of the receiver.

Referring now to FIG. 8, the mono/biphasic control 56 and the channel enable logic 60 circuits are shown. More specifically, the mono/biphasic control circuit 56 comprises flip-flop 148. The mono/biphasic programming data Qm is applied to the reset line of flip-flop 148 via conductor 54 from flip-flop 120 of the shift register 42 in FIG. 6. The clock input of the flip-flop 148 is the inverted transmitted pulse $\overline{V}p$ which is provided by NAND gate 89 of FIG. 4. The data input of flip-flop 148 is connected to the inverted $\overline{Q}$ output of the flip-flop 148. The inverted $\overline{Q}$ and non-inverted Q outputs of flip-flop 148 are routed to the output control logic circuit of FIG. 9 via conductor bus 57.

As stated above, when monophasic operation occurs, the relative polarity of the stimulated electrodes remains constant throughout the stimulation mode. In the biphasic mode, however, this polarity alternates with each stimulation pulse. For example, if electrodes 18a and 18c are to be stimulated, and electrode 18a is to have positive polarity while electrode 18c a negative polarity; then during the biphasic mode, the polarity of these two electrodes will reverse with every stimulation pulse such that electrode 18a will be negative and electrode 18c will be positive.

In operation of the mono/biphasic control circuit 56, the inverted signal $\overline{V}p$ causes clocking at the end of the stimulation pulse since the flip-flop 148 is clocked with a rising edge. If the mono/biphasic bit Qm of the programming data 28 is logic low, which indicates monophasic mode, then the non-inverted Q output of flip-flop 148 will be logic high. The inverted $\overline{Q}$ output of flip-flop 148 will be logic low and this signal will be applied to the data input flip-flop 148. Since the flip-flop 148 is not reset every transmitted pulse, its outputs remain constant. However, should the mono/biphasic control bit be logic high, which indicates biphasic mode, then the inverted $\overline{Q}$ output of flip-flop 148 will be a logic high. This signal is applied to the data input of flip-flop 148. The non-inverted Q output of the flip-flop 148 will be a logic low. On each subsequent trammsitted pulse, the flip-flop 148 will be reset since the bit Qm is logic high. Therefore, the outputs of the flip-flop 148 will alternate logic states. These outputs are routed via conductor bus 57 to the output control logic circuit of FIG. 9.

The channel enable logic circuit 60 is also shown in FIG. 8. This circuit comprises NAND gates 150-157. NAND gate 156 is the control gate and provides a logic low output only when the following conditions occur simultaneously: (a) the proper channel has been selected; (b) four consecutive, identical programming data sequences have been received by the error detection circuit 66 of FIG. 7; and (c) no invalid electrode combinations which would short the receiver have been selected. More specifically, the channel enable function is selected by NAND gates 150-153. In the preferred embodiment of the invention, it is desired that two redundant receivers will be present in the same receiver package. The use of two receivers provides greater flexibility in that the second receiver may be used for a different set of electrodes or as a backup should the initial receiver become defective.

In operation, each of the receivers includes a pin which will be grounded or tied to a positive voltage, depending on whether it will be designated channel A or B. This connection is applied via conductor 158 to the inputs of NAND gates 150 and 151. The other input of NAND gate 151 is the programming data bit $Q_E$ from the non-inverted Q output of flip-flop 121 of shift register 42 in FIG. 6. The signal on conductor 158 is inverted by NAND gate 150 and applied to one input of NAND gate 152. The other input of NAND gate 152 is the programming data bit $\overline{Q}_E$ from the inverted $\overline{Q}$ output of flip-flop 121 of shift register 42 in FIG. 6. Assuming that receiver A is to be utilized, conductor 158 will be tied to a positive voltage and the programming data bit $\overline{Q}_E$ will be logic high. Therefore, the output of NAND gate 150 will be logic low and the output of NAND gate 152 will be logic high. However the output of NAND gate 151 will be logic low and therefore the output of NAND gate 153 will be logic high, indicating a channel has been selected. If receiver B is to be utilized, conductor 158 will be tied to ground and the programming data bit $\overline{Q}_E$ will be logic high. Therefore, the outputs of NAND gates 150 and 152 will be logic high and low, respectively. Since the output of NAND gate 152 is low, the output of NAND gate 153 is high and a channel has been selected. This output is applied to control NAND gate 156.

The output of the error detection circuit 66 of FIG. 7 is routed via conductor 68b to another input of NAND gate 156. This output will be logic high whenever four consecutive, identical programming data sequences have been received. The final input of control NAND gate 156 is from the output control logic circuit 52 of FIG. 9 via conductor 64. In particular, a low signal on this conductor indicates that an invalid electrode polarity combination has been selected for one of the electrodes by the physician. This low signal is applied to one input of NAND gate 154. The other three inputs of NAND gate 154 are derived from the output control logic of the other three electrodes. If an invalid combination is selected, the output of NAND gate 154 is logic high. This signal is inverted by NAND gate 155 to disable the control NAND gate 156. If no invalid combinations have been selected for each electrode, the output of NAND gate 155 is logic high. Therefore, since all the inputs of NAND gate 156 are logic high, its output is logic low. This signal is inverted by NAND gate 157 and applied via conductor 63 to the output control logic circuit 52 of FIG. 9. Therefore, a logic high signal on conductor 63 indicates that (a) the proper channel has been selected, (b) four consecutive and identical programming data sequences have been received, and (c) no invalid electrode combinations have been selected. This logic high signal indicates that the receiver is now in the stimulation mode.

Figure 9:
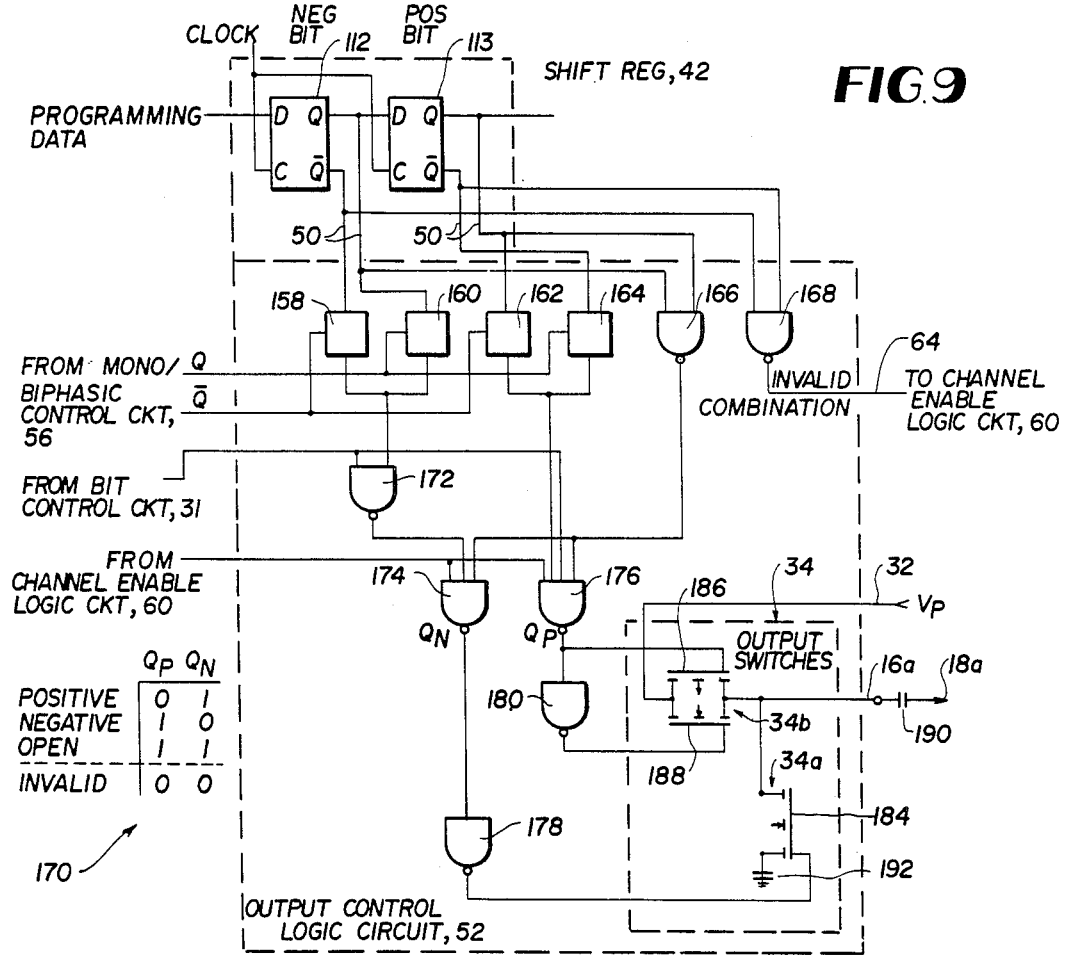
FIG. 9 shows a schematic diagram of the output control logic circuit and output switches of the receiver for one of the electrodes.

Turning now to FIG. 9, the output control logic 52 and the output switches 34 for one of the electrodes 18 is shown. It should be noted that the output control logic for the other three electrodes 18 will be identical to the circuit seen in FIG. 9, except they will have inputs from different flip-flops of the shift register 42 of FIG. 6. In operation, two programming data bits from each set of programming data 28 control each electrode 18. The use of two bits allows each electrode to assume a positive, negative or open circuit status with respect to the other electrodes. More specifically, if the negative polarity control bit Qn is stored in one of the flip-flops 112-121 of shift register 42 of FIG. 6, the positive polarity control bit Qp is stored in the next succeeding flip-flop. The flip-flops provide non-inverted and inverted outputs of the positive and negative polarity bits which are routed via conductor bus 50 to the output control logic circuit 52. The control bits may be put in any convenient order other than that described above.

Referring now specifically to FIG. 9, the output control logic for electrode 18a is provided. For this electrode, the negative and positive programming data bits are stored in flip-flops 112 and 113, respectively, of shift register 42. The negative and positive programming data bits for the other three electrodes are stored in flip-flops 114–121 of shift register 42 in FIG. 6. The inverted output $\overline{Q}n$ of flip-flop 112 is applied to a gated switch 158 and to one input of a NAND gate 168. The non-inverted output Qn of flip-flop 112 is applied to gated switch 160 and to one input of a NAND gate 166. The non-inverted output Qp of flip-flop 113 is applied to gated switch 162 and to the other input of NAND gate 168. The inverted output $\overline{Q}p$ of flip-flop 113 is applied to gated switch 164 and the second input of NAND gate 168. The output of NAND gate 166 will always be logic high unless the electrode is to be left open. The output of NAND gate 168 is applied via conductor 64 to the channel enable logic circuit of FIG. 8 to indicate whether an invalid electrode combination has been selected. With reference to truth table 170, this condition occurs whenever both the non-inverted Q outputs of flip-flops 112 and 113 are logic low.

The gated switches 158, 160, 162 and 164 are controlled by the output of the mono/biphasic control circuit 56 of FIG. 8. In particular, the inverted $\overline{Q}$ output of flip-flop 148 of the mono/biphasic control circuit 56 is applied as the gate signal to gated switches 158 and 162. Also, the non-inverted Q output of flip-flop 148 is applied as the gate signal to gated switches 160 and 164. When the gate signal is logic high, the input to the gated switch is transmitted to the output of the gated switch.

The outputs of gated switches 158 and 160 are coupled to one input of NAND gate 172. The other input to NAND gate 172 is provided via conductor 51 by the bit counter circuit such that this gate is only turned on after ten data bits have been received. The output of NAND gate 172 is applied as one input to a negative control NAND gate 174. The other inputs to negative control NAND gate 174 are provided by the channel enable logic circuit 60 of FIG. 8 via conductor 63, and the output of NAND gate 166. The outputs of gated switches 162 and 164 are coupled to one input of a positive control NAND gate 176. The other inputs of this positive control NAND gate are provided by the channel logic circuit 60 via conductor 63, the output of NAND gate 166, and from the bit counter circuit 31 via conductor 51. The output of negative control NAND gate 174 is Qn in truth table 170 and is applied to output switch 34a and to NAND gate inverter 178. The output of positive control NAND gate 176 is Qp in truth table 170 and is applied to output switch 34b and to NAND gate inverter 180.

The output switch 34a comprises a n-channel MOS transistor 184 while output switch 34b comprises p-channel MOS transistor 186 and n-channel MOS transistor 188. The transmitted pulse $V_P$ can be applied to the electrode 18a via conductor 32 if the electrode has a programmed positive polarity. This pulse is coupled to electrode 18a by capacitor 190.

The operation of the output control logic 52 in FIG. 9 can be best explained by example. Assuming that electrode 18a is to have a positive polarity, then Qp is logic low and Qn is logic high as defined by truth table 170. Further, assume that monophasic capability is required such that the non-inverted Q output of flip-flop 148 in FIG. 8 is logic high and the inverted $\overline{Q}$ output is logic low. Recall that in the monophasic mode, these outputs will remain constant. Finally, it is assumed that (a) bit counter circuit 31 of FIG. 2 has determined that ten data bits have been received such that a logic high is present, on conductor 51, and (b) the channel enable logic circuit 60 of FIG. 8 has been enabled such that a logic high is present on conductor 63.

Under these conditions, the flip-flop 112 will have a logic high at its non-inverted Q output and a logic low at its inverted $\overline{Q}$ output. Further, the non-inverted Q output of flip-flop 113 will be logic low and the inverted $\overline{Q}$ output will be logic high. Since the monophasic mode is programmed, the non-inverted Q output of flip-flop 148 of FIG. 8 will gate a logic high through both gated switch 160 and gated switch 164. Gated switches 158 and 162 will not be enabled since the inverted $\overline{Q}$ output of the flip-flop 148 of FIG. 8 is logic low. Ssince the bit counter circuit 31 has provided a logic high output via conductor 51, the output of NAND gate 172 is a logic low signal which is applied to negative control NAND gate 174. The output of NAND gate 166 is logic high since electrode 18a is being programmed for receiving the stimulation pulse. Since the channel enable logic circuit of FIG. 8 has been enabled, all the inputs to positive control NAND gate 176 are logic high, and thus the output of this gate is logic low. Further, since a logic low is present at negative control NAND gate 174, the output of this gate is logic high.

The logic low signal from positive control NAND gate 176 is applied to the p-channel MOS transistor 186 of output switch 34b and to the NAND gate inverter 180. The output of the NAND gate is a logic high which turns the n-channel MOS transistor 188 of switch 34b ON. Similarly, the logic low signal turns ON p-channel MOS transistor 186. Since the output of the negative control NAND gate 174 is logic high, the output of NAND gate invertor 178 is logic low. This logic low signal holds n-channel MOS transistor 184 of switch 34a OFF, thereby disconnecting the electrode from ground 192. Therefore, since transistors 186 and 188 of switch 34b are ON and transistor 184 of switch 34a is OFF, the pulse $V_p$ is applied through output switch 34b and capacitor 190 to the electrode 18a.

Assume now that the physician requires the electrode 18a to have a negative or grounded polarity. In this case the output of negative control NAND gate 174 is logic low and the output of positive control NAND gate 176 is logic high. Therefore, n-channel MOS transistor 184 is ON, and the electrode 18a is pulled to ground potential 192. Note that the stimulation pulse cannot be transmitted through output switch 34b since both p-channel MOS transistor 186 and n-channel MOS transistor 188 are OFF.

It should be noted that if the channel enable logic circuit 60 is not enabled, as would occur if the proper channel has not been selected, four consecutive, identical data sequences haven't been received, or an invalid electrode has been selected, a logic low is present on conductor 63. This signal causes both Qn and Qp to be logic high and thus the electrode will be open. This open condition will also occur if a logic low is present on conductor 51, indicating that the bit counter 31 has not counted ten data bits.

Finally, should the physician require biphasic stimulation in the example above wherein electrode 18a is positive the outputs of the flip-flop 148 of FIG. 8 will alternate with each stimulation pulse. This alternation causes gated switches 158 and 162 to be enabled each time the outputs of flip-flop 148 in FIG. 8 alternate. The outputs of the switches 158 and 162 is a logic low signal which causes the outputs of the negative and positive control NAND gates 174 and 176 to alternate with each stimulation pulse. Therefore electrode 18a will go from positive polarity to ground and back again during three stimulation cycles. This cycling will continue as long as the mono/biphasic programming data bit is logic high.

The other electrodes 18b-18d can be programmed in a similar manner. Therefore, it can be seen that the receiver circuitry of the present invention provides a unique electronic system wherein the implanted electrodes can be independently programmed by the physician. In particular, each electrode is capable of dynamically assuming a positive, negative or open circuit status any time after implantation. This flexibility gives the physician an improved opportunity to attain a desired result with less inconvenience to the patient.

Although the preferred embodiment is shown to have four electrodes and ten data bits, it should be recognized that this should not be considered limiting. Any number of data bits and electrodes may be utilized.

Figure 16:
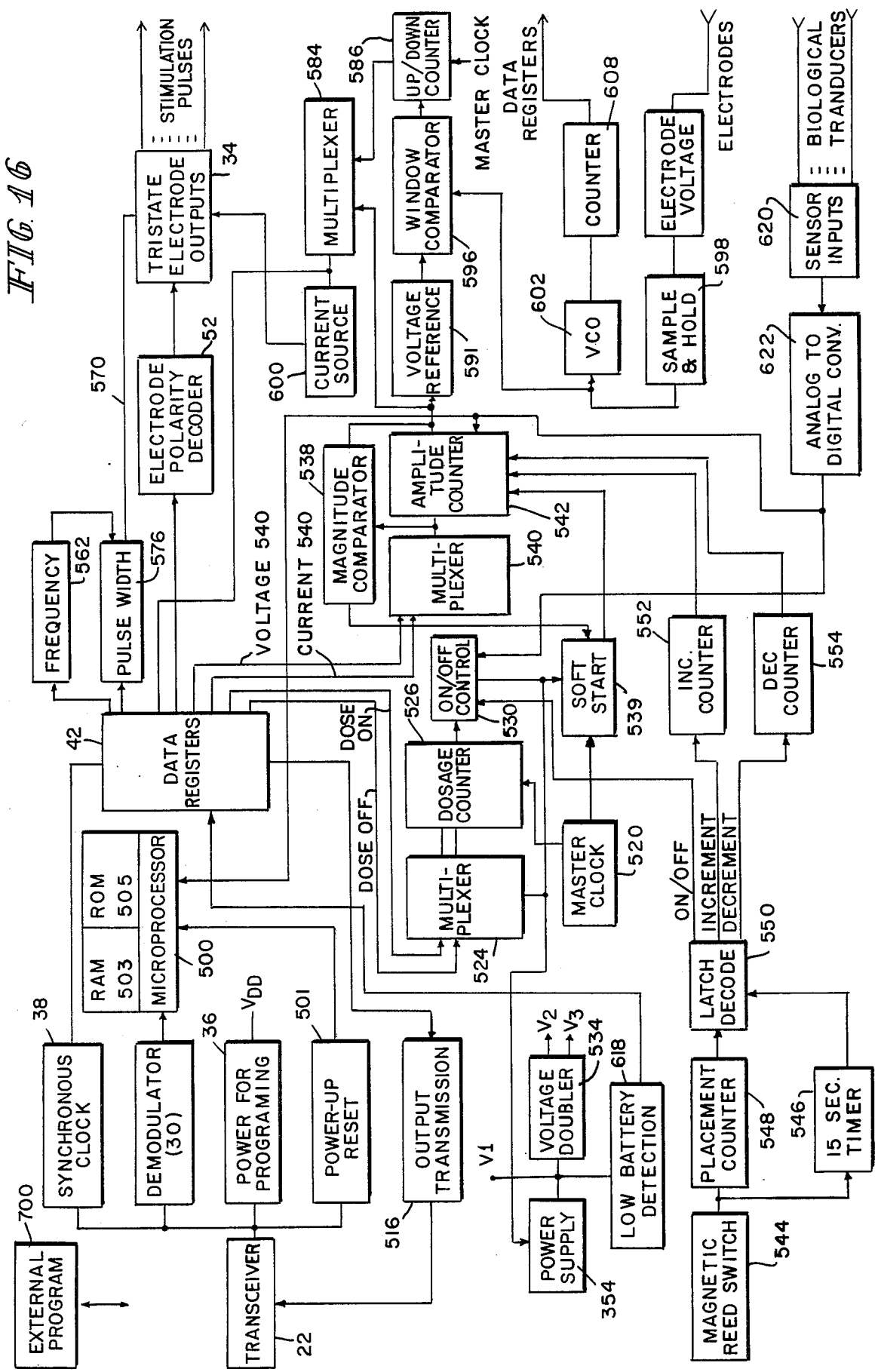
FIG. 16 is a block diagram of a unitary implantable transceiver stimulator.
Figure 11:
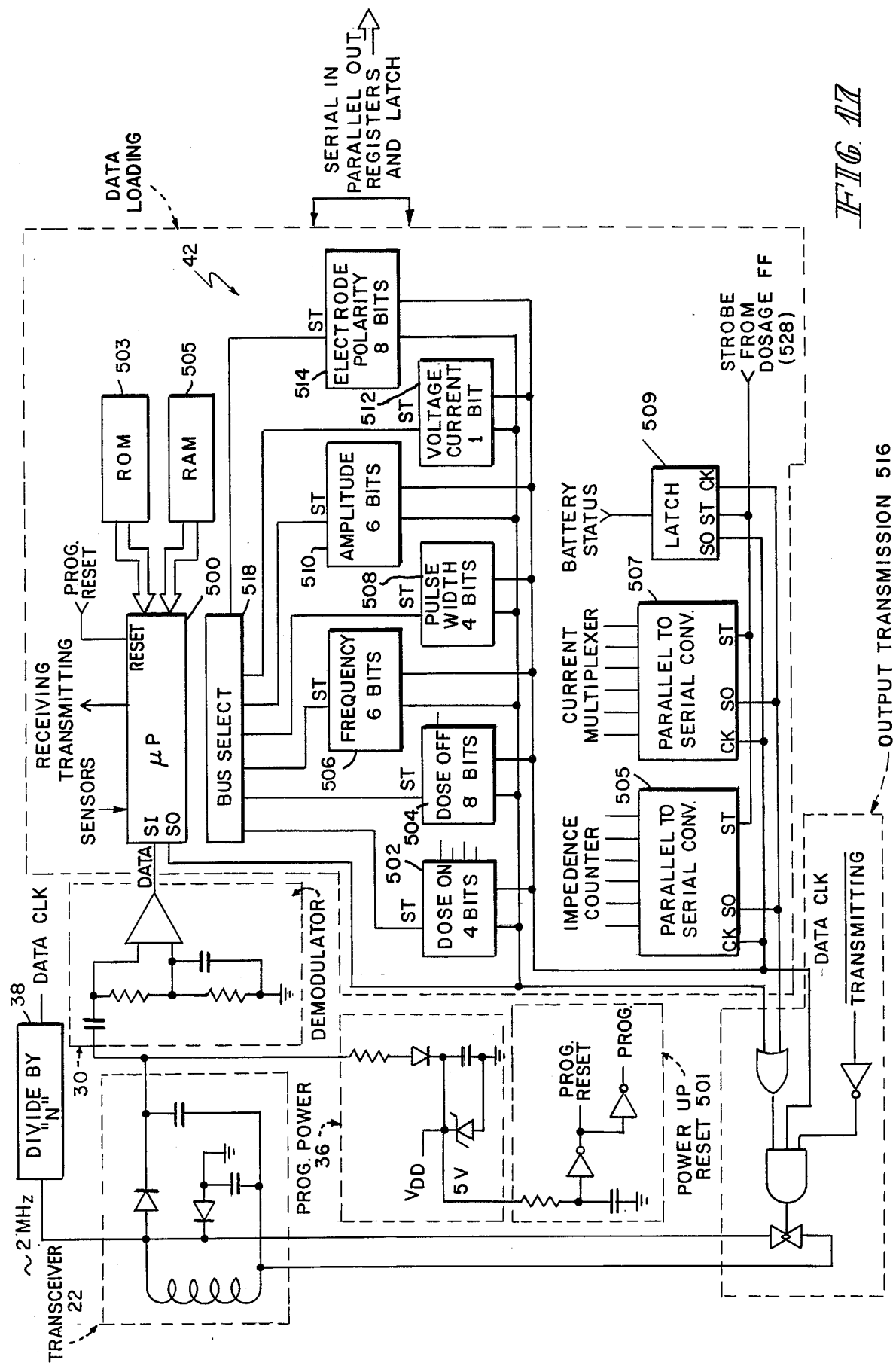

The stimulator of FIG. 16 is a totally implanted, multiprogrammable tissue stimulator with telemetry. Via a radio frequency transmission link frequency, amplitude, waveform, pulsewidth, dosage and electrode polarities can be programmed by external programmer 700. Voltage and current sourced outputs may also be chosen. The parameter values are telemetered from the implant to the external programmer, as well as model and serial numbers, electrode impedance and the battery status. The patient may alter the amplitude plus or minus two or more increments via an external handheld magnet. It should be noted that those elements of the totally implanted embodiment performing similar functions have the same number as used in the embodiment of FIG. 2.

Using a 2 MHz carrier, an antenna coil in transceiver 22, receives data signals. A comparator 30 demodulates the signal producing binary coded data which is serially loaded into a data latch 42 under the control of microprocessor 500. The continuous 2 MHz carrier frequency is rectified at 36 to produce the necessary power for the programming circuitry. The output of the transceiver 22 is also provided to synchronize data clock 38 and power up reset 501 which provides programming and programming reset signals to the microprocessor 500. The microprocessor 500, under control of a program stored in ROM 503 and RAM 504 determines from the first three bits into which data register latch 502-514 of FIG. 17 to load the incoming data via bus select 518. Each register and latch 502-514 has a serial input, parallel outputs, to respective latches, and serial outputs to output transmission 516. The data registers and latches include Dose on 502, Dose off 504, Frequency 506, Pulsewidth 508, Pulse Amplitude 510, Voltage/current 512 and Electrode polarity 514. Other register latches may be provided for other parameters. Additional output data is provided for output transmission by impedance parallel to serial converter 505, current parallel to serial converter 507 and battery status latch 509. The RAM 504 may have its processing program changed by the external programmer 700. At the onset of the programming procedure the circuitry is powered by the rectified carrier (alternately it is powered from the internal power source) 36 and the implant transmits all parameter values to the programmer. The microprocessor 500 follows a preset sequence as it controls the serial output transmission 516 performed by loading and unloading of the receiver coil corresponding to each bit state. The data is detected by the programmer 700 monitoring changes in amplitude of the 2 MHz carrier signal. When a specific parameter is being programmed, the word is received and then transmitted back to the programmer 700 which verifies that the data was transmitted properly. A positive verification bit from the programmer 700 latches the respective data with a strobe signal from the bus select 518.

Other telemetry means may be used, for example that of U.S. Pat. No. 4,223,679. In addition, data can be telemetered to the external programmer 700 between receiving stimulation piulse in the FIG. 2 configuration.

Figure 24:
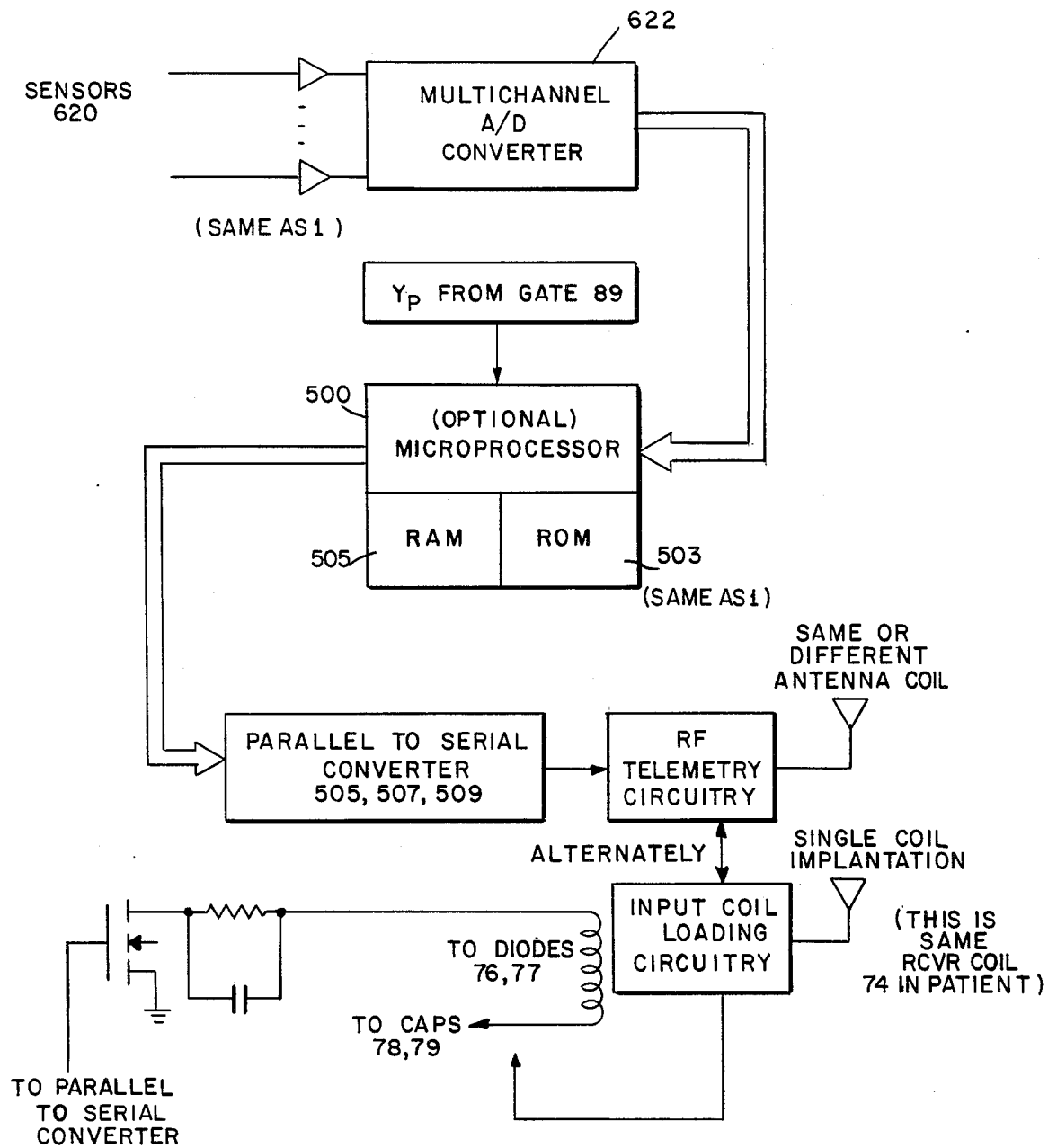
FIG. 24 is a block diagram of a telemetry system for use with the implant of FIG. 2.

The input coil loading circuitry version of FIG. 24 would require a microprocessor or dedicated logic and timing circuitry. The microprocessor 500 gets its input Vp from gate 89 and FIG. 4. This signal goes high in between the transmitted RF bursts. This signal will be used to trigger the microprocessor 500 to sequentially perform the following tasks:

1. Perform an A-D conversion update from the sensors 620.
2. Run the programs specified in RAM 50A and ROM 503 using the new data.
3. Deliver a parallel output of the results of the measurements to parallel-to-serial converters 505-509.

The output of the parallel-to-serial converter 505-509 goes to the input coil loading circuitry as pulses. These pulses load the coil and are picked up by the external transmitter using the same circuitry described in the antenna locator circuit of the transmitter including 218, 219, 220, 221, 222, described earlier. Although the Vp signal described above is generated between the large RF bursts, it should be made clear that the transmitter actually continues to transmit a very low level RF signal, which is loaded and unloaded and from which the data is discerned at the transmitter/programmer. Alternately the microprocessor 500 may be eliminated and logic circuitry substituted to perform the functions described above. The microprocessor and/or other logic could then be put into the external transmitter/programmer. Circuitry could be provided in the external transmitter/programmer to respond to this data equivalent to the circuitry described earlier in the implant itself.

A simple system would monitor, in the implant, physiological parameters to be measured and produce a tone or other signal allowing a patient or physician to manually alter the programs.

Figure 18:
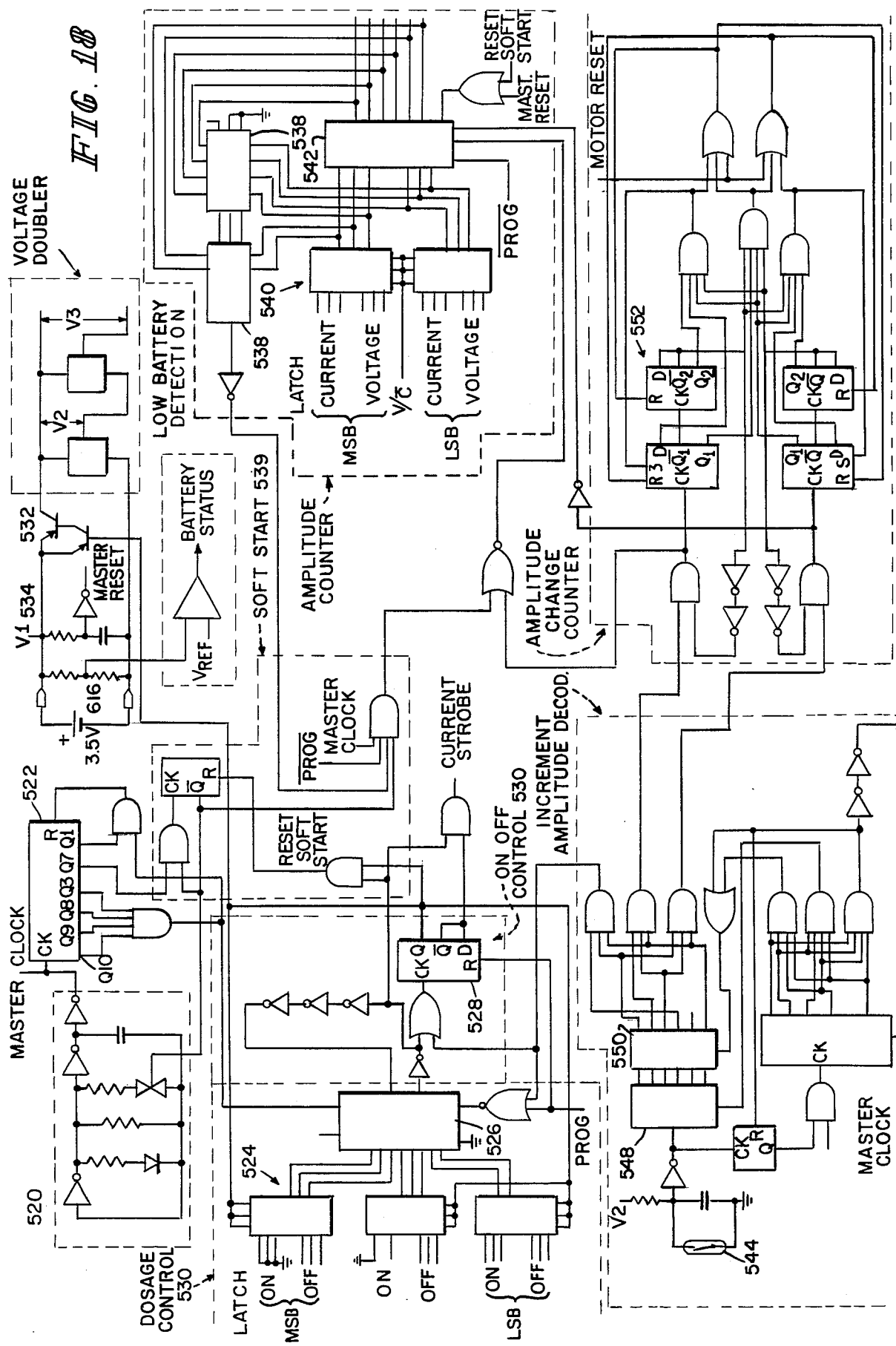
FIG. 18 is a schematic of the master clock, Dosing, soft start, amplitude control with increment/decrement and hour battery circuits.

The master clock 520 of FIG. 18, a common conventional inverter configuration, operates at 1 Hz or 5 Hz. A divide by "N" counter 522 produces a pulse every fifteen minutes. The dosage data from register/latches 502 and 504, which is the binary code for the number of quarter hours desired, is multiplexed by multiplexer 524 into a dose counter 526. When zero is reached, the D-flip flop 528 of ON/OFF control 530 changes states, selecting the new dosage data (i.e., if going off to on, it will select the dosage on data) and loads it into the same counter. When the flip flop 528 is in the off state "1", the only components powered are the data latches 502-514, the master clock 520 and the dosage control circuitry 523, 524, 526. The high output turns off the darlington transistor pair 532 and all but the battery voltage 534 is disabled. Although specific timing is mentioned it is not meant to be limiting.

At the onset of "dose on", it is necessary to ramp up the output amplitude. The master clock 520 is increased to operate at 5 Hz via an alteration in the RC network values 536, and for a maximum of 15 seconds, and clocks an up counter 542. The counter output is compared via magnitude comparators 538 to the amplitude binary code from multiplexors 540. When they are equal (A=B) the counting is inhibited. After the 15 seconds the master clock 520 returns to operation at 1 Hz. During programming the soft start circuit 539 is disabled and the respective amplitude value is loaded directly into the counter.

The placement of an external magnet over the implant will close a reed switch 544 and start a timer 546. The user must place and displace the magnet one, two or three times within a predetermined time period (for instance 10 seconds). The number of times is counted by placement counter 548 and latched by latch decoder 550.

System Codes:
One=ON/OFF (the opposite of the present state)
Two=increase the amplitude by one increment
Three≦decrease the amplitude by one increment Two increments are allowed in either direction. It is obvious that any allowable number of increments or codes can be designed in. The placement counter 548 is decoded, latched and cleared after 12 seconds. The latch 550 is strobed again at 14 seconds producing a pulse which is input to the clock of a two bit counter, which the code is to increase or decrease. Each function has its own counter 552, 554. If the respective count of the two bit counter is less than three then a clock pulse is input to the amplitude up/down counter 542. If the two counters are equal (both are 1) they are reset. If one counter is two and the other is one, each are decremented one count. At the onset of "dose on" all counters are reset and the amplitude counter 542 is loaded with the programmed value from registers 510 and 512 via multiplexer 540.

The battery voltage 534 is compared to a reference voltage 616 at the onset of programming. The output from the comparator 618 is transmitted to the programmer 700 via latch 509 of FIG. 17. A "1" indicates that the battery voltage has depleted below the reference point and three months of battery life remain.

The frequency circuit 562, of FIG. 19, via the use of a current mirror 556 produces different currents controlled by selector 558 and 560 as determined by the binary coded frequency data from register 506. The current values, selected by different resistor values, are binary weighted to eliminate the need for decoding. The current charges a capacitor 564, whose voltage is compared to a reference voltage by comparator 566. When the capacitor voltage exceeds the reference voltage an output transition occurs. The capacitor 564 is then discharged by switch 568 under the control of flip flop 572 and the cycle repeats producing a current controlled oscillator. The larger the current the faster the capacitor charges, therefore the output frequency 570 will be faster.

The output transmission from the current controlled oscillator 562 alternate the state of a D flip flop 572. A resistor-capacitor network 574 is used to reset the flip flop at a selected time constant. The pulse width data bits from register 508 select the resistor combination 578 to produce the desired pulse width in pulse width circuit 576.

The current source 600 of FIG. 20 using a current mirror 580 and resistor selectors 581 and 583 produce 1/100th of the output current desired. The currents are designed to be binary weighted, which eliminates the need for decoding. This current is multiplied by 100 at 585 and delivered to the output stages 534. The data is input from the multiplexed bits 584 of the amplitude counter 542 of FIG. 18 or the voltage source counter 586.

The binary code from the amplitude counter 542, which has the voltage amplitude data loaded into it, also controls resistor selectors 587 and 589 in a current mirror circuit 588 to produce voltages across a 100k resistor 590 in 0.25 V increments. A 0.25 V reference is added at comparator 592 and subtracted at comparator 594 to the established voltage. These voltages are the references of the window comparator 596 for the measured output voltage from the electrode impedance sample and hold circuit 598. This comparison determines whether to count the output counter 586 up or down (increasing or decreasing amplitude accordingly). The count outputs are sent to the current source 600 and select the necessary current to produce the desired voltage.

The electrode voltage is buffered and placed into a sample and hold circuit 598. A fixed current charges a capacitor 604 in a voltage controlled oscillator 602, which, for a preset amount of time determined by timer 607, is counted by counter 608, producing an impedance equivalent binary code for the measured voltage. This binary number 612 is latched along with the value of the current 610, and when transmitted to the programmer 700 via parallel to serial converters 505 and 507 of FIG. 17, can be used to calculate the impedance.

The electrode output switches 34 are controlled by a two bit code for each of the four electrodes:
00=off
01=anode
10=cathode
Note this is different from the two bit code of FIG. 9.

Figure 21:
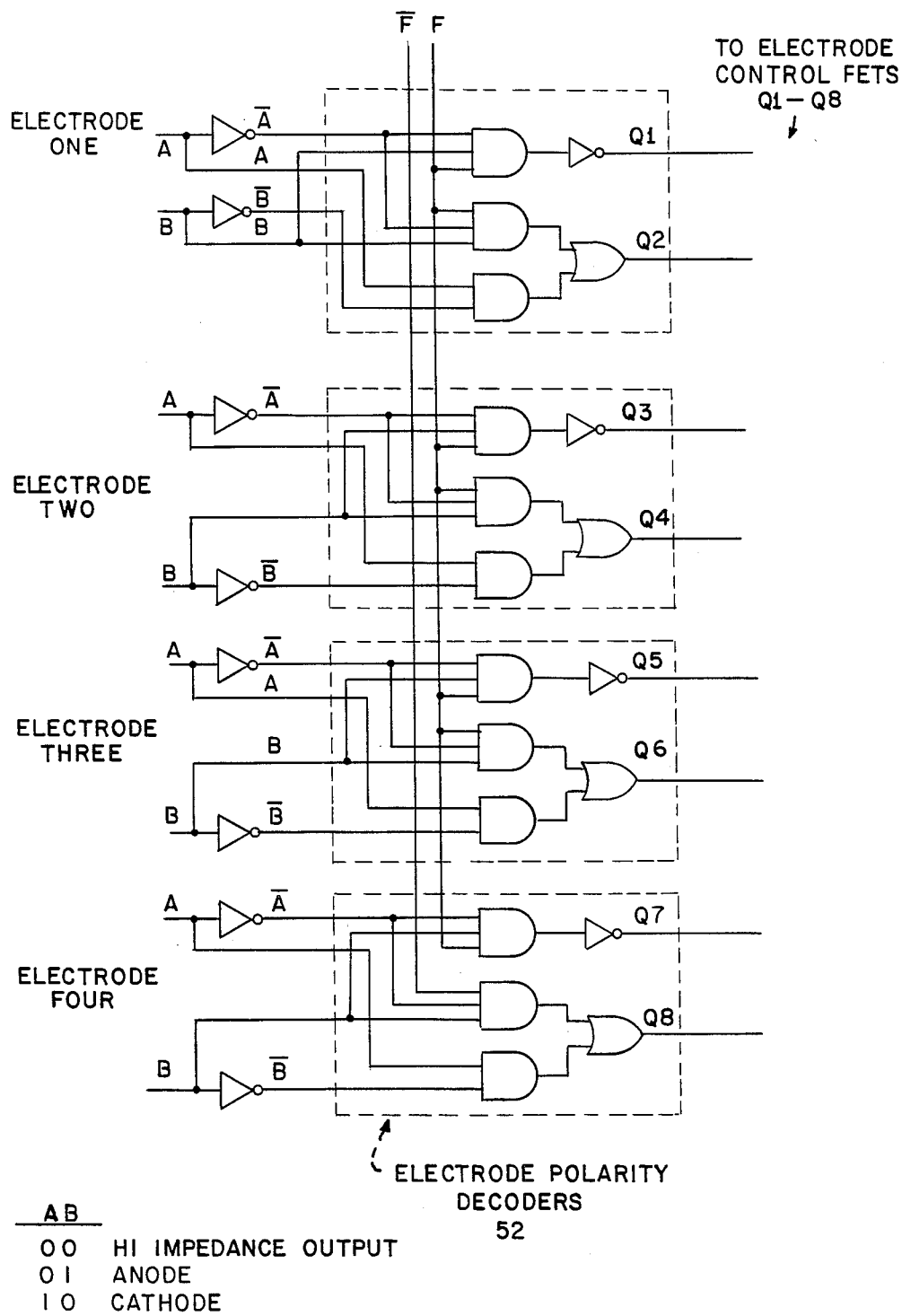
FIG. 21 is a schematic of the electrode polarity decoder.

Using low on-resistance FET's ($Q_1$-$Q_8$), the polarity configuration of the electrodes is controlled by polarity decoder 52 of FIG. 21 and data from register 514 of FIG. 17. A P-chanhnel FET ($Q_1$, $Q_3$, $Q_5$, $Q_7$) connects the electrode to the output source and an N-channel FET ($Q_2$, $Q_4$, $Q_6$, $Q_8$) connects the electrode to ground. Both are off when the electrode is off. When the electrode is to be the cathode the respective N-channel FET is on. When the anode is the polarity chosen the respective P-channel is turned on and off by the frequency and pulsewidth output 570. During the off state the N-channel FET is turned on to discharge the coupling capacitors 614.

Via sensors 620 in the implant and an analog to digital converter 622 in FIG. 16, the stimulation parameters can be actively controlled. Also logarithmic waveforms can be produced by ramping up the amplitude based on the present amplitude state measured by different sensors. This is similar to the soft start control and the voltage source control, as only control signals are different.

Also microprocessor control is shown to be possible since the sensors digitally encoded output is provided to the microprocessor 500.

Figure 22:
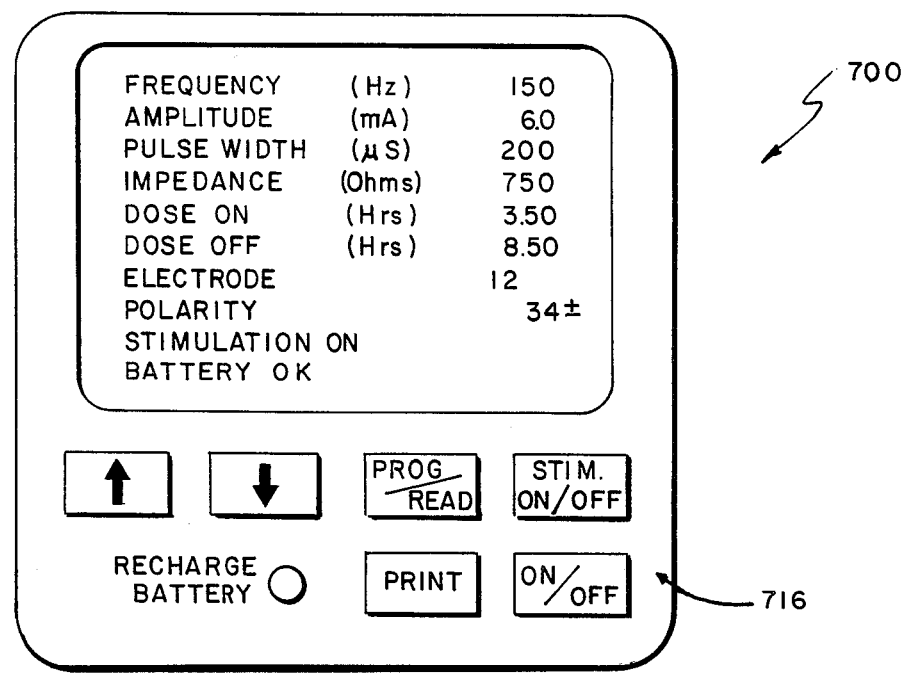
FIG. 22 is a front view of the face of an external programmer.

The external programmer 700 for a totally implanted multiprogrammable tissue stimulator, via a radio frequency transmission link, transmits frequency, pulsewidth, dosage and electrode polarities data. Voltage and current source outputs may also be chosen. Displayed are all parameter values, electrode impedance and the battery status. The face of the programmer 700 is illustrated in FIG. 22.

Figure 23:
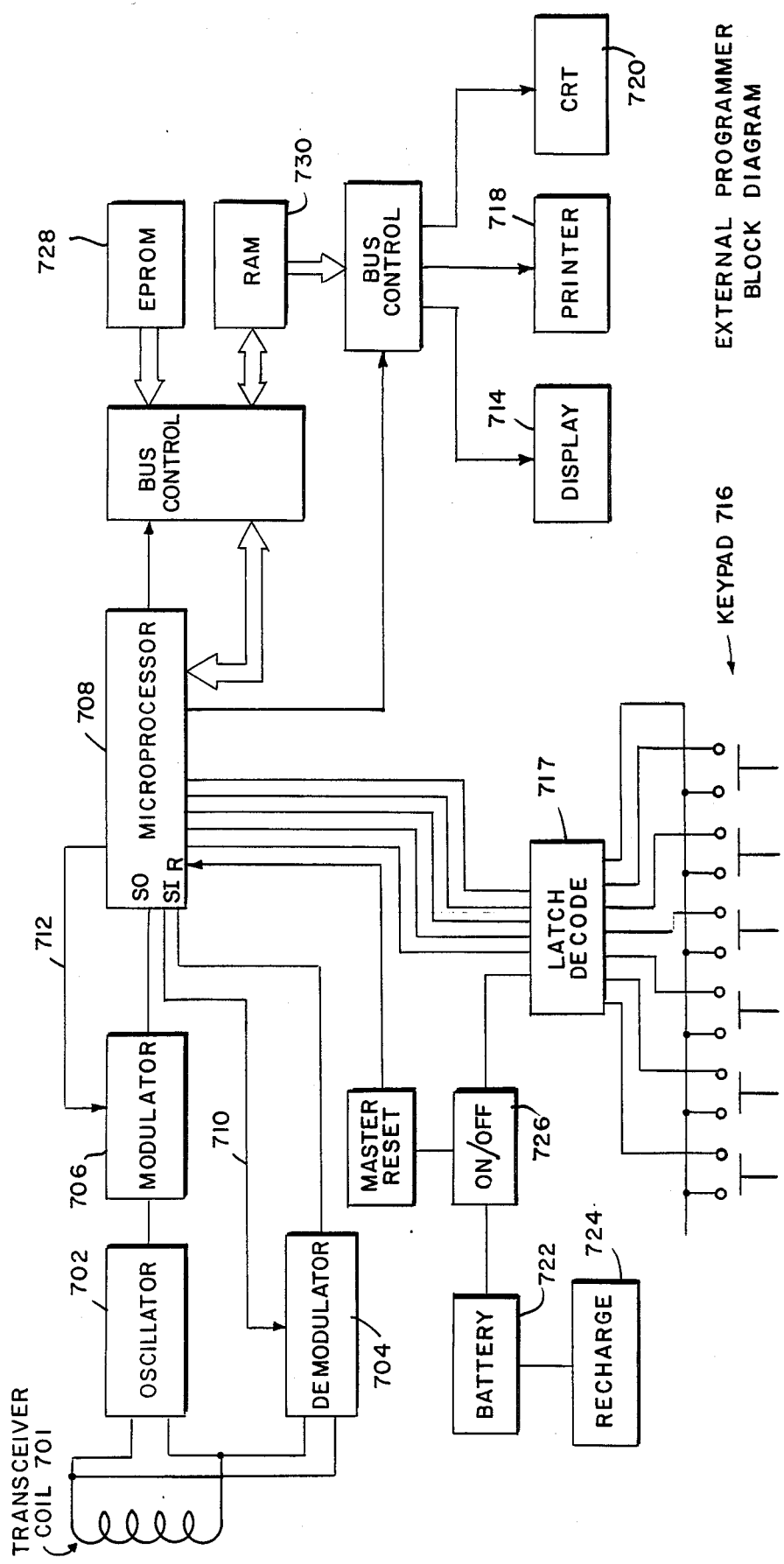
FIG. 23 is a schematic of an external programmer.

The transmission link consists of the transceiver coil 701, the oscillator 702, modulator 706, and demodulator 704. When the device is turned on by keyboard 726 as illustrated in FIG. 23, the oscillator 720 is turned on and supplies a carrier frequency (nominally 2MHz). The microprocessor 708 activates the demodulator 704 and begins sampling the amplitude of the carrier frequency. If the signal is received by the implant, the implant will proceed to transmit all of its parameter values at a lower rate, 1 KHz for example. The microprocessor 708 decodes the data words and loads them into the appropriate locations in RAM 730 via bus control 729. Once loaded into RAM 730, the data will be on display 714. When a parameter value is to be programmed, the demodulator 704 is disabled via 710 and the modulator is enabled via 712. The data is serially loaded into the modulator 706 and transmitted to the implant by oscillator 702. The implant will transmit the word back to the programmer 700, which has now activated the demodulator 704, and the programmer compares the word to the data it transmitted. If they are the same, a verification code is sent to the implant. If not, the data is retransmitted.

The microprocessor program is stored in an EEPROM 728. In this memory are programs for calculations, transmission sequencing, lock up tables, data decoding, default conditions, user warnings and peripheral device driver instructions. To someone skilled in the art, it can be seen there is no limit to the stored function capabilities.

Via the RAM 730, all data accumulated after the device has been turned on may be displayed. With a liquid crystal display 714 and membrane key pad 716, the following information is presented:

Frequency
Amplitude
Pulsewidth
Impedance
Dose On
Dose Off
Electrode Polarity
Stimulation state (on or off)
Battery o.k. or Change Battery
Optional-pressure, Flow, pH, etc. (not shown)

This by no means limits the data that may be displayed, i.e., battery life remaining, sensor in use, waveform, etc.

The data may also be delivered to any peripheral device such as a printer 718 or CRT 720.

The parameters are displayed in their respective units, i.e., frequency is displayed in Hertz.

"Change Battery" indicates a fixed period of time until full battery depletion.

The programmer is powered by a 7.2 V NiCd battery 722. The battery may be recharged 724 via an EMF method or a direct coupled method.

Figure 26:
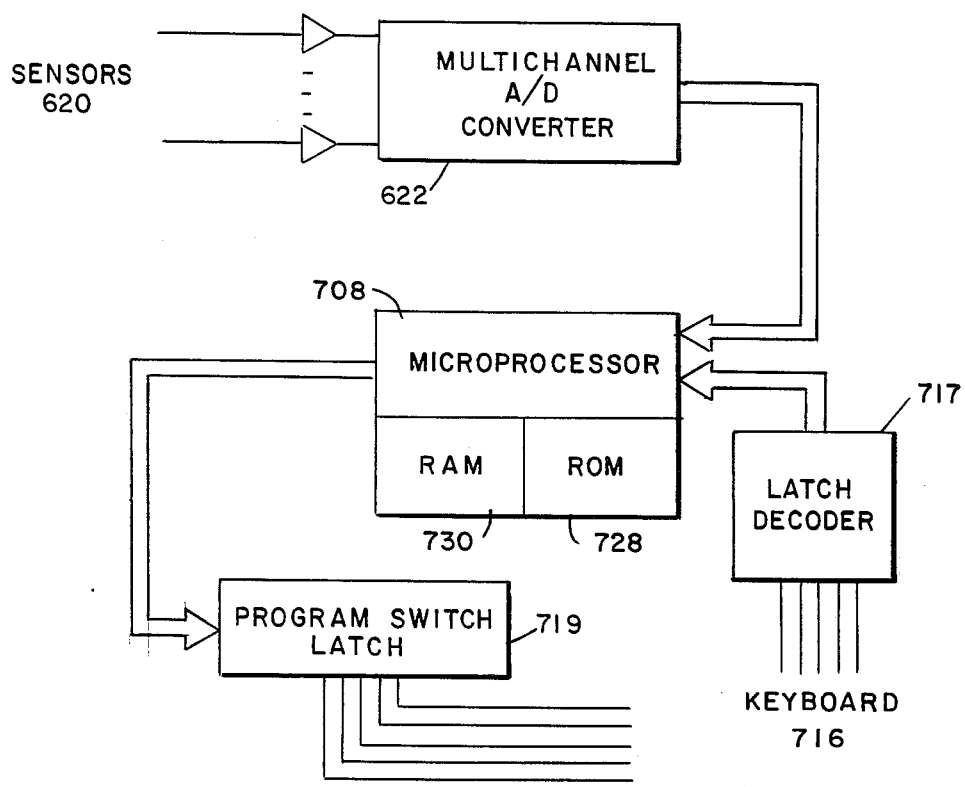
FIG. 26 is a block diagram of a modification of FIG. 23 for external measurement processing.

As an alternative to performing the sensing and stimulation alteration internally, this process may be performed by the external programmer 700. As illustrated in FIG. 26, external programmer 700 includes sensor inputs 620, multichannel A-D 622 and microprocessor 708 with stored programs in ROM 728 and received programs in RAM 730. Input programming switches from the keyboard 716 to the latch decoder 717 are combined with sensor information. The microprocessor 708 yields an output as a result of programming and input data. Digital outputs are fed to an output latch 719 which is updated and refreshed under microprocessor control. The output of the program switch latch 719 goes to the latch decoder 717 inputs.

This type of circuit diagram is useful for auditory and visual prosthesis in particular but also might be used in conjunction with the internally measured parameters of the embodiment of FIG. 2. The circuit of FIG. 24, the implanted portion, could be simplified such that no microprocessor need be in the implant. The transmitted information would go to the external transmitter by some form of telemetry link which would alter the program accordingly.

In addition, the same scheme could be used for RESPIRATORY STIMULATION. In particular, internal parameters such as blood gases and/or lung pressure, etc., and external factors such as skin temperature, perspiration, etc. would be monitored. Respiratory stimulation is primarily performed by stimulation of the phrenic nerve and the ideal product would be a total implant with an internal power source and closed loop feedback based on some internally measured physiological parameter.

A similar scheme may be used for BLADDER STIMULATION. Bladder stimulation can be effected by stimulating the sacral nerves or via direct stimulation of the bladder. In some instances, it is also necessary to simultaneously stimulate the sphincter muscle and/or the innervating nerve(s). Sensors including an ultrasonic sensor to determine residual urine in the bladder could be combined with this embodiment. Again, the ideal product would be a totally implanted unit with internal power source but with an external unit to effectuate voiding and/or the internal ability to provide an electrical "tickle" which the patient would sense to know that they should prepare for voiding.

The instant invention thus provides an efficient tissue stimulation system for controlling nervous or muscular disorders. In particular, the system can be used to stimulate the cervical area of the spinal cord, the brain, the cerebellum or individual nerve fibers or bundles to elicit motor, sensory, neurologic, physiologic or psychological responses. Alternatively, the system may be used to control muscle disorders, such as heart ailments. It is also envisioned that this system be utilized whenever stimulation is required for any other therapeutic reason.

Another specific application would be monitoring blood pressure and stimulating specific nerves around the heart to vary blood pressure.

Another potential application is a biochemical sensor to sense chemicals such as neurotransmitters, blood sugar level, pH, hormones etc. and, electrically stimulating various organs, glands or nerves to maintain proper levels of same in the body.

An implantable auditory sensor for a totally implantable artificial ear is another application. The sensor would be processed through the circuitry and then automatically stimulate either nerves or the cochlea. Alternatively, an external sensor using the same technology as the visual prosthesis of FIG. 28 except having an audio sensor is illustrated in FIG. 29.

For the visual or auditory prosthesis a high frequency transmission link could be used which removes the necessity of placing the transmitter and receiver antennas in juxtaposed, close proximity. Also, the ability to perform bipolar stimulation or any set or combination of electrodes allows reduction of the number of electrodes needed.

Some specific applications of using sensors to modify stimulators would include implanting an intercranial pressure monitor as a sensor and applying electrode cuffs to various nerves such as the carotid artery to alter blood flow to the brain.

Figure 27:
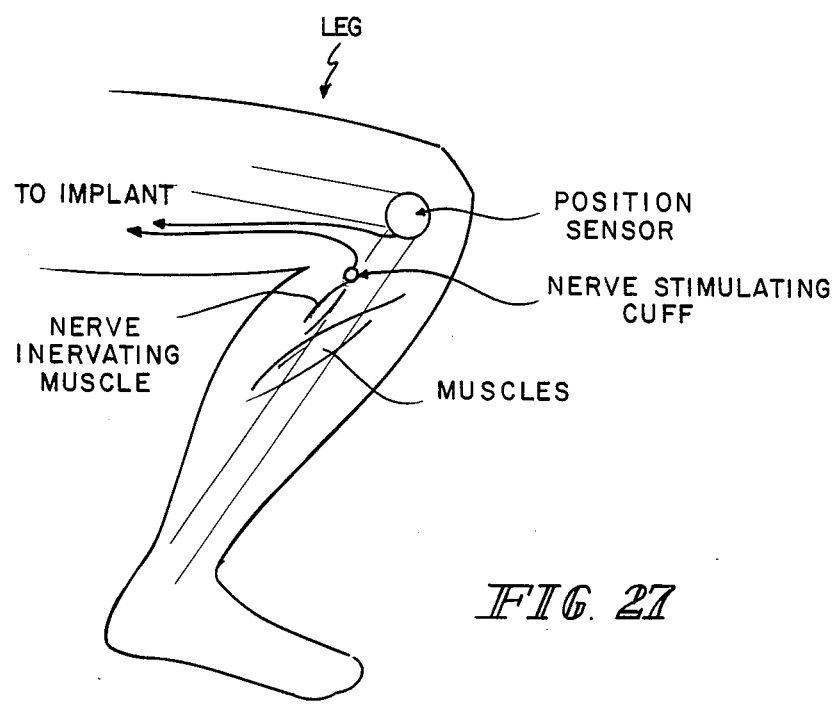
FIG. 27 is a diagram of a stimulator used with a prosthesis.

A position sensor could be used in a number of different applications. One such application would be in paraplegic or spinal cord injury patients where position sensors could be placed at various joints and on certain muscles and/or ligaments as illustrated in FIG. 27. These sensors would provide a closed loop system for stimulating the nerves and muscles. The result could be development of a total closed loop implantable prosthesis. This might ultimately allow ambulation or the ability to perform functions such as raising your arm or feeding yourself, etc.

Figure 28:
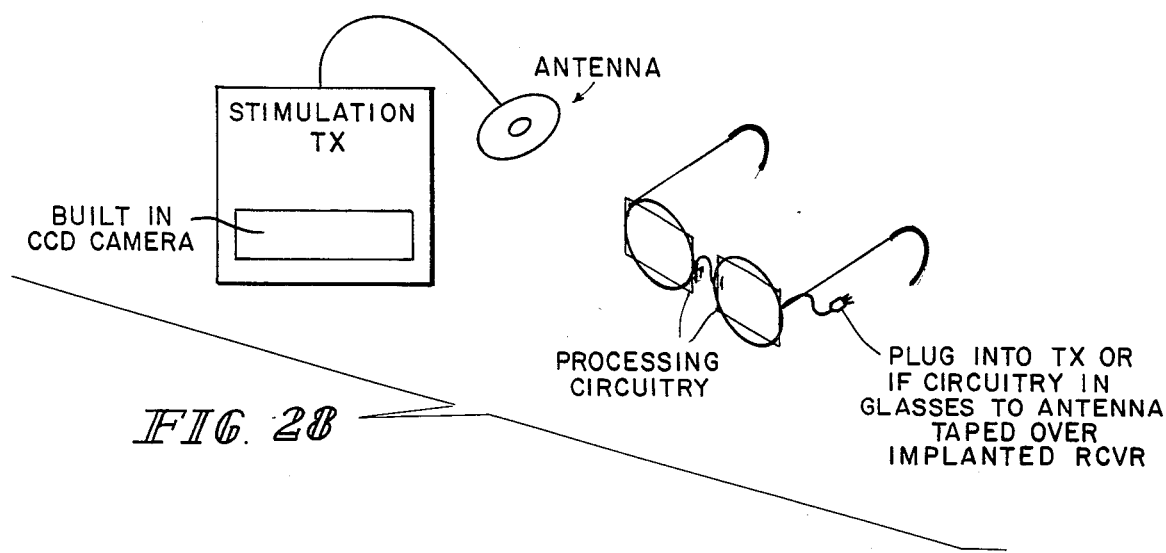
FIG. 28 is a diagram of a visual prosthesis.
Figure 29:
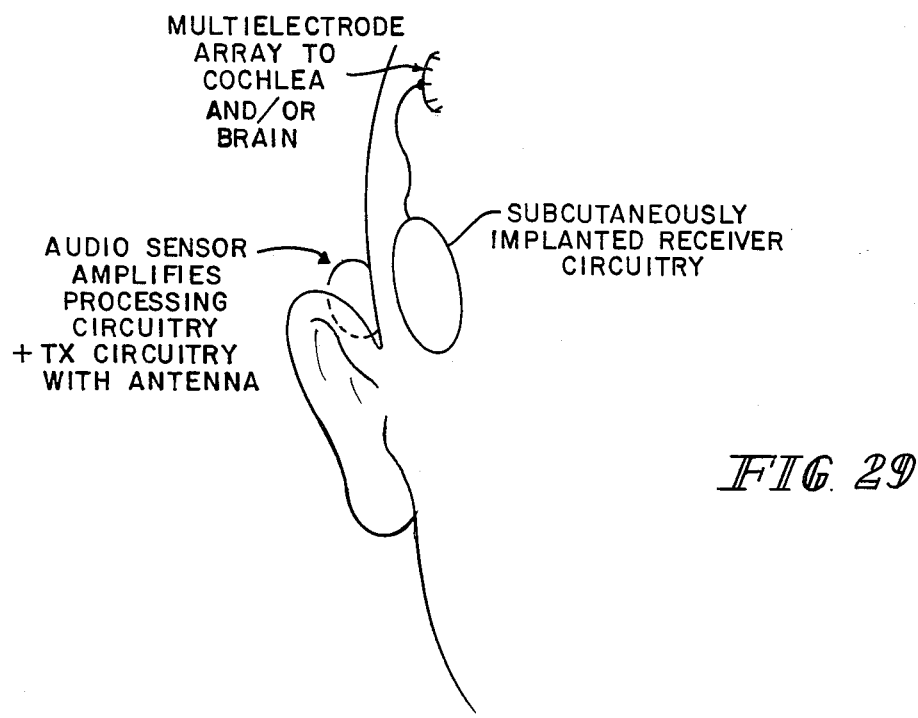
FIG. 29 is a diagram of an auditory prosthesis.

An implantable visual prosthesis is also a possibility using an implanted CCD (camera) array and analog amplifiers that compensate for the effects of tissue filtering on the received image as illustrated in FIG. 28. A CCD camera would be in the transmitter on a belt or the pair of glasses connected to the transmitter. The glasses could also include transmitter circuitry. The implanted electrodes may be placed on a large area of a cortical surface or nerve cuff or cuffs on the optic nerve(s). Preferably, the electrodes are arranged in a matrix or grid to increase the ability to produce the desired results. Also, the ability to perform multipolar stimulation is provided.

It is anticipated that developments by the medical community will enable measurement of certain physiological parameters to determine the optimum stimulation parameters. The instant invention includes the concept of incorporating measurement circuitry into the implant for telemetry to assist in determining the best therapeutic regimen. The invention further includes incorporation of a mircroprocessor or logic circuitry into the implant to automatically reprogram stimulation parameters.

From the preceding description of the preferred embodiments, it is evident that the objects of the invention are attained, and although the invention has been described and illustrated in detail, it is to be clearly understood that the same is by way of illustration and example only and is not to be taken by way of limitation. The spirit and scope of the invention are to be limited only by the terms of the appended claims.

What is claimed is:

1. An electronic tissue stimulator system, comprising:
   at least three electrodes to be implanted adjacent tissue to be stimulated in a patient;
   transmitting means for transmitting programming data to define for each of said electrodes to a positive, negative or high impedance state;
   receiving means to be surgically implanted within said patient for receiving said programming data, for generating stimulation pulses and for delivering said stimulation pulses to said electrodes having positive and negative states as defined by said programming data;
   means for automatically measuring physical parameters; and
   means for modifying said programming data as a function of said sensed parameters.

2. An electronic tissue stimulator system as defined in claim 1 including means for measuring physiological parameters.

3. An electronic tissue stimulator system as defined in claim 1 including means for measuring electrode impedance and means for modifying said stimulation pulses or said defined electrodes as a function of said measured impedance.

4. An electronic tissue stimulator system as defined in claim 1 wherein said measuring means is in said receiving means for transmitting said measured parameters to said transmitting means.

5. An electronic tissue stimulator system as defined in claim 1 wherein said measuring means and said receiving means includes means for transmitting said measured parameters to said transmitting means.

6. An electronic tissue stimulator system as defined in claim 1 wherein said measuring means and said modifying means are in said receiving means.

7. An electronic tissue stimulator system as defined in claim 1 wherein said modification means is an implanted microprocessor.

8. An electronic tissue stimulator system as defined in claim 7 wherein said microprocessor includes memory means storing programs.

9. An electronic tissue stimulator system as defined in claim 8 wherein said microprocessor includes means for loading programs received from said transmitting means.

* * * * *